(12) United States Patent
Neikirk et al.

(10) Patent No.: US 11,174,552 B2
(45) Date of Patent: *Nov. 16, 2021

(54) ROTARY REACTOR FOR UNIFORM PARTICLE COATING WITH THIN FILMS

(71) Applicant: Applied Materials, Inc., Santa Clara, CA (US)

(72) Inventors: Colin C. Neikirk, Sunnyvale, CA (US); Pravin K. Narwankar, Sunnyvale, CA (US); Kaushal Gangakhedkar, San Jose, CA (US); Visweswaren Sivaramakrishnan, Cupertino, CA (US); Jonathan Frankel, Los Gatos, CA (US); David Masayuki Ishikawa, Mountain View, CA (US); Quoc Truong, San Ramon, CA (US); Joseph Yudovsky, Campbell, CA (US)

(73) Assignee: Applied Materials, Inc., Santa Clara, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 16/438,371

(22) Filed: Jun. 11, 2019

(65) Prior Publication Data

US 2019/0376181 A1    Dec. 12, 2019

Related U.S. Application Data

(60) Provisional application No. 62/683,763, filed on Jun. 12, 2018.

(51) Int. Cl.
*C23C 16/455* (2006.01)
*C23C 16/44* (2006.01)
*C23C 16/442* (2006.01)

(52) U.S. Cl.
CPC ...... *C23C 16/45544* (2013.01); *C23C 16/442* (2013.01); *C23C 16/4417* (2013.01); *C23C 16/45578* (2013.01)

(58) Field of Classification Search
None
See application file for complete search history.

(56) References Cited

U.S. PATENT DOCUMENTS 3,818,982 A    6/1974   Wagner
6,613,383 B1   9/2003   George et al.
(Continued)

FOREIGN PATENT DOCUMENTS

WO    WO 2007/123510    11/2007
WO    WO 2014/044907    3/2014

OTHER PUBLICATIONS

PCT International Search Report and Written Opinion in International Appln. No. PCT/US2019/036721, dated Oct. 10, 2019, 9 pages.

*Primary Examiner* — Karla A Moore
(74) *Attorney, Agent, or Firm* — Fish & Richardson P.C.

(57) ABSTRACT

A reactor for coating particles includes one or more motors, a rotary vacuum chamber configured to hold particles to be coated, wherein the rotary vacuum chamber is coupled to the motors, a controller configured to cause the motors to rotate the rotary vacuum chamber about an axial axis of the rotary vacuum chamber such that the particles undergo tumbling agitation, a vacuum port to exhaust gas from the rotary vacuum chamber, a paddle assembly including a rotatable drive shaft extending through the rotary vacuum chamber and coupled to the motors and at least one paddle extending radially from the drive shaft, such that rotation of the drive shaft by the motors orbits the paddle about the drive shaft in a second direction, and a chemical delivery system including (Continued)

a gas outlet on the paddle configured inject process gas into the particles.

21 Claims, 14 Drawing Sheets

(56) References Cited

U.S. PATENT DOCUMENTS

| | | |
|---|---|---|
| 2004/0052984 A1 | 3/2004 | Toth |
| 2011/0116984 A1* | 5/2011 | Rehmat .................. C10J 3/005 422/184.1 |
| 2011/0200822 A1* | 8/2011 | Detavernier .......... C23C 16/458 428/402 |
| 2012/0145041 A1* | 6/2012 | Walters ................. B82Y 30/00 106/472 |
| 2013/0059073 A1* | 3/2013 | Jiang ................ C23C 16/45561 427/212 |
| 2014/0127756 A1 | 5/2014 | Bolz et al. |
| 2015/0125599 A1 | 5/2015 | Lindfors et al. |
| 2017/0346077 A1 | 11/2017 | Kamo et al. |
| 2018/0019468 A1* | 1/2018 | Zhu .................... H01M 4/8867 |
| 2018/0221294 A1 | 8/2018 | Carlsson et al. |
| 2019/0376182 A1 | 12/2019 | Neikirk et al. |

* cited by examiner

ROTARY REACTOR FOR UNIFORM PARTICLE COATING WITH THIN FILMS

CROSS-REFERENCE TO RELATED APPLICATIONS

This application claims priority to U.S. Provisional Patent Application Ser. No. 62/683,763, filed on Jun. 12, 2018, the disclosure of which is incorporated by reference.

TECHNICAL FIELD

This disclosure pertains coating particles, e.g., particles that include active pharmaceutical ingredients, with thin organic and inorganic films.

BACKGROUND

It is of great interest to the pharmaceutical industry to develop improved formulations of active pharmaceutical ingredients (API). Formulation can influence the stability and bioavailability of the API as well as other characteristics. Formulation can also influence various aspects of drug product (DP) manufacture, for example, ease and safety of the manufacturing process.

Numerous techniques for encapsulating or coating API have been developed. Some existing techniques for the coating of API include spray coating, plasma polymerization, hot wire chemical vapor deposition (CVD), and rotary reactors. Spray coating is an industrially scalable technique that has been widely adopted by the pharmaceutical industry. However, coating non-uniformities (both within a particle and from particle to particle) prevent the use of these techniques for improving the delivery profile or stability of active pharmaceutical ingredients (APIs). Particle agglomeration during spray coating also causes significant challenges. Meanwhile, techniques such as plasma polymerization are difficult to scale, applicable only to certain precursor chemistries, and can result in the degradation of sensitive APIs. Hot wire systems have been developed that utilize a cold substrate as the condensation media for gases and radicals. Rotary reactors include atomic layer deposition (ALD) and initiated CVD (iCVD) reactors. However, ALD reactors are suitable for inorganic coatings and not for organic polymer coatings, and existing iCVD designs do not adequately prevent API degradation and are not scalable for high volume manufacturing. Other techniques include polymer mesh coating, pan coating, aerosolized coating, and fluidized bed reactor coating.

SUMMARY

In general, one innovative aspect of the subject matter described in this specification can be embodied in a reactor for coating particles that includes one or more motors, a rotary vacuum chamber configured to hold multiple particles to be coated, a cylindrical portion of the rotary vacuum chamber having an inner diameter, and where the rotary vacuum chamber is coupled to the one or more motors to rotate the rotary vacuum chamber in a first direction about an axial axis of the cylindrical portion of the rotary vacuum chamber, a vacuum port to exhaust gas from the rotary vacuum chamber, a paddle assembly including a rotatable drive shaft extending through the rotary vacuum chamber along the axial axis of the rotary vacuum chamber and at least one paddle extending radially from the drive shaft, where the rotatable drive shaft is coupled to the one or more motors such that rotation of the drive shaft by the one or more motors orbits the at least one paddle about the drive shaft in a second direction, and a chemical delivery system configured to inject a process gas into the particles, where the at least one paddle includes a gas outlet of the chemical delivery system to inject the process gas into the particles.

Implementations may include one or more of the following features. In some implementations, rotation in the first direction is in a same direction of rotation as the rotation in the second direction, e.g., clockwise or counter-clockwise.

In some implementations, the gas outlet of the chemical delivery system is located on a trailing edge of the at least one paddle.

In some implementations, a vacuum port is located in-line with the axial axis of the rotary vacuum chamber.

In some implementations, the at least one paddle is one of multiple paddles configured to sweep along an entirety of a length of the rotary vacuum chamber along the axial axis of the rotary vacuum chamber. The at least one paddle can further include an anti-static brush located between an outer edge of the paddle and in contact with the surface of the inner diameter of the rotary vacuum chamber.

In some implementations, the reactor further includes a port to deliver particles to or receive particles from the rotary vacuum chamber.

In some implementations, the axial axis of the rotary vacuum chamber is oriented horizontally relative to gravity.

In general, another aspect of the subject matter described in this specification can be embodied in a reactor for coating particles that includes one or more motors, a rotary vacuum chamber configured to hold multiple particles to be coated, a cylindrical portion of the rotary vacuum chamber having an inner diameter, and where the rotary vacuum chamber is coupled to the one or more motors, a controller configured to cause the one or more motors to rotate the rotary vacuum chamber in a first direction about an axial axis of the cylindrical portion of the rotary vacuum chamber at a rotation speed sufficient to force the multiple particles to be centrifuged against the inner diameter of the rotary vacuum chamber, a vacuum port to exhaust gas from the rotary vacuum chamber, a paddle assembly including a rotatable drive shaft extending through the rotary vacuum chamber along the axial axis of the rotary vacuum chamber and at least one paddle extending radially from the drive shaft, where the rotatable drive shaft is coupled to the one or more motors such that rotation of the drive shaft by the one or more motors orbits the at least one paddle about the drive shaft in a second direction, and a chemical delivery system configured to inject a process gas into the particles, where the at least one paddle includes a gas outlet of the chemical delivery system to inject the process gas into the particles.

In some implementations, the controller is configured to cause the one or more motors to rotate the rotary vacuum chamber about the axial axis at the rotation speed that is greater than 15 RPM. The rotation speed of the drive shaft relative to the rotary vacuum chamber about the axial axis can be at least 4 rpm.

In some implementations, the reactor further includes a base to support the reactor on a mounting surface, and where the rotary vacuum chamber is secured to the base such that the axial axis will be perpendicular to the mounting surface.

In some implementations, rotation in the first direction is in an opposite direction of rotation as the rotation in the second direction.

In some implementations, the at least one paddle includes a rake-shaped feature including multiple tines such that the tines of the paddles are in contact with the particles when the chemical delivery system is injecting the process gas into the particles. The gas outlet of the chemical delivery system can be located on a trailing edge of at least one tine of the multiple tines of the rake-shaped features of the paddle. An outer edge of the paddle can be separated from a surface of the inner diameter of the rotary vacuum chamber by a gap, e.g., a 1-3 mm gap.

In some implementations, the at least one paddle includes a T-shaped feature including a segment parallel to the surface of the inner diameter of the rotary vacuum chamber.

In general, another aspect of the subject matter described in this specification can be embodied in methods that include the actions of dispensing particles into a rotary vacuum chamber, rotating the rotary vacuum chamber along an axial axis of the rotary vacuum chamber in a first direction such that the particles form a toroid on an inner wall of the rotary vacuum chamber, evacuating the chamber through a vacuum port in the rotary vacuum chamber aligned on the axial axis of the rotary vacuum chamber, rotating a paddle assembly in a second direction such that multiple paddles orbit a drive shaft, injecting a process gas into the particles through multiple gas outlets located on the multiple paddles.

In some implementations, the methods comprise coating the particles by atomic layer deposition or molecular layer deposition.

In general, another aspect of the subject matter described in this specification can be embodied in a reactor that includes one or more motors, a rotary vacuum chamber configured to hold multiple particles to be coated, a cylindrical portion of the rotary vacuum chamber having an inner diameter, and where the rotary vacuum chamber is coupled to the one or more motors, a controller configured to cause the one or more motors to rotate the rotary vacuum chamber in a first direction about an axial axis of the cylindrical portion of the rotary vacuum chamber at a rotation speed such that the particles undergo tumbling agitation, a vacuum port to exhaust gas from the rotary vacuum chamber, a paddle assembly including a rotatable drive shaft extending through the rotary vacuum chamber along the axial axis of the rotary vacuum chamber and at least one paddle extending radially from the drive shaft, where the rotatable drive shaft is coupled to the one or more motors such that rotation of the drive shaft by the one or more motors orbits the at least one paddle about the drive shaft in a second direction, and a chemical delivery system configured to inject a process gas into the particles, where the at least one paddle includes a gas outlet of the chemical delivery system to inject the process gas into the particles.

In some implementations, the controller is configured to cause the one or more motors to rotate the rotary vacuum chamber about the axial axis at the rotation speed that is less than 6 rpm. The rotation speed of the drive shaft relative to the rotary vacuum chamber about the axial axis can be selected such that the relative motion of the paddles 158 within the powder does not cause milling and/or damage to the powders during the rotary motion(s) of the rotary vacuum chamber and paddle assembly.

In some implementations, the reactor further includes a stationary vacuum chamber, where the rotary vacuum chamber is disposed within the stationary vacuum chamber.

In some implementations, the reactor further includes a vacuum pump coupled to the stationary vacuum chamber and coupled to the vacuum port to exhaust gas from the rotary vacuum chamber. The chemical delivery system and the one or more motors can be coupled to the stationary vacuum chamber.

In some implementations, the rotary vacuum chamber further includes a surface of the inner diameter of the rotary vacuum chamber having horizontal or angled baffles.

In general, another aspect of the subject matter described in this specification can be embodied in methods that include the actions of dispensing particles into a rotary vacuum chamber, rotating the rotary vacuum chamber along an axial axis of the rotary vacuum chamber in a first direction such that the particles fill a lower portion of the rotary vacuum chamber when the rotary vacuum chamber is rotating in the first direction, evacuating the chamber through a vacuum port in the rotary vacuum chamber aligned on the axial axis of the rotary vacuum chamber, rotating a paddle assembly in a second direction such that multiple paddles orbit a drive shaft, and injecting a process gas into the particles through multiple gas outlets located on the multiple paddles.

In some implementations, the methods include coating the particles by atomic layer deposition or molecular layer deposition.

In some implementations, the particles include a core containing a drug.

In some implementations, the rotary vacuum chamber is configured to perform initiated chemical vapor deposition.

In some implementations, the methods further include depositing an organic or inorganic coating over the particles. The organic or inorganic coating can be an inorganic metal oxide. The organic or inorganic coating can be an organic polymer.

Implementations may include, but are not limited to, one or more of the following possible advantages. Particles, e.g., API particles, can be coated with in a high volume manufacturing process, thereby providing lower cost of manufacturing and reduced drug product prices. Particles can be coated with thin layer(s), thus providing a drug product with an advantageous volume fraction of API. In addition, the process can result in layer(s) encapsulating the API that are uniform within a particle and from particle-to-particle, providing more consistent properties to the drug formulations.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

Other features and advantages of the invention will be apparent from the following detailed description and figures, and from the claims.

BRIEF DESCRIPTION OF THE DRAWINGS

FIG. 2 can be taken along line Q-Q in FIG. 1.

FIG. 5 can be taken along line Q-Q in FIG. 4.

Like reference numbers and designations in the various drawings indicate like elements.

DETAILED DESCRIPTION

Figure 1:
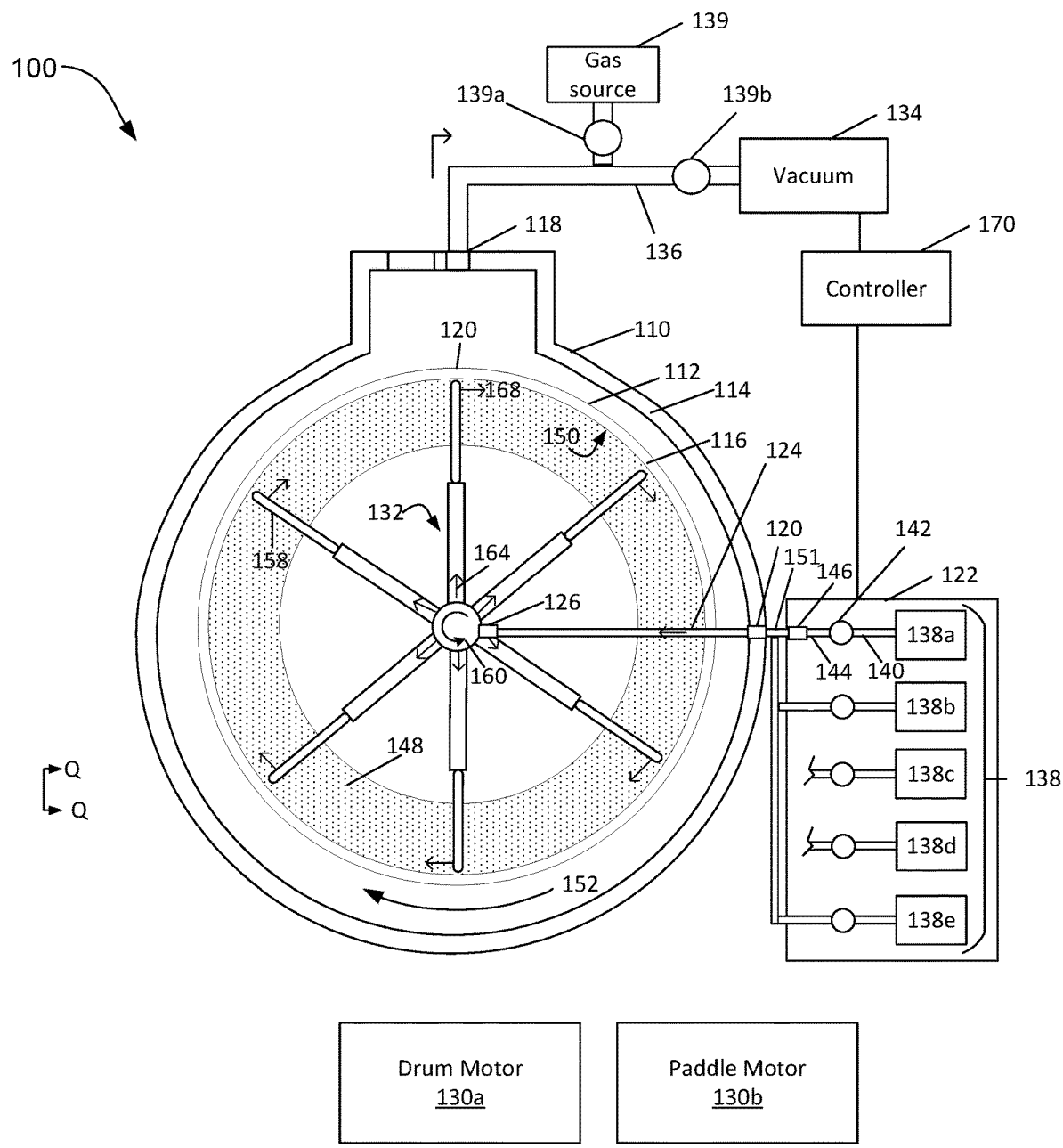
FIG. 1 is a schematic front view of an example reactor for ALD and/or CVD coating of particles, e.g., drugs, that includes a rotary vacuum chamber.

There are various methods for encapsulating API particles. In many cases, these methods result in a coating that is relatively thick. While such coatings can impart desirable properties, the high ratio of coating to API can make it difficult to create a drug product in which the volume fraction of API is as high as desired. In addition, the coating encapsulating the API can be non-uniform, making it difficult to provide formulations with consistent properties. Furthermore, coating techniques that can provide satisfactory consistency have not be scalable for industrial manufacturing.

An approach that may address these issues is to use a rotary "drum" in which particles are centrifuged against an inner wall of the rotary drum through rotary motion of the drum in a first direction, and in which paddles rotating in a second direction (e.g., a same or an opposite direction as the first direction) agitate the particle bed. Process gas can be injected into the particle bed through gas outlets located on the paddles. This can force process gas to percolate through the particle bed, which can improve uniformity of coating across particles.

Another approach that may address these issues is to use a rotary vacuum chamber "drum" in which particles are agitated both by a rotation of the rotary vacuum chamber and by paddles of a paddle assembly that is rotating with respect to the rotary vacuum chamber, and where process gas is injected into the particles through gas outlets located on the paddles. This can force process gas to percolate through the particles, which can improve uniformity of coating across particles.

Drug

The term "drug," in its broadest sense includes all small molecule (e.g., non-biologic) APIs. The drug could be selected from the group consisting of an analgesic, an anesthetic, an anti-inflammatory agent, an anthelmintic, an anti-arrhythmic agent, an antiasthma agent, an antibiotic, an anticancer agent, an anticoagulant, an antidepressant, an antidiabetic agent, an antiepileptic, an antihistamine, an antitussive, an antihypertensive agent, an antimuscarinic agent, an antimycobacterial agent, an antineoplastic agent, an antioxidant agent, an antipyretic, an immunosuppressant, an immunostimulant, an antithyroid agent, an antiviral agent, an anxiolytic sedative, a hypnotic, a neuroleptic, an astringent, a bacteriostatic agent, a beta-adrenoceptor blocking agent, a blood product, a blood substitute, a bronchodilator, a buffering agent, a cardiac inotropic agent, a chemotherapeutic, a contrast media, a corticosteroid, a cough suppressant, an expectorant, a mucolytic, a diuretic, a dopaminergic, an antiparkinsonian agent, a free radical scavenging agent, a growth factor, a haemostatic, an immunological agent, a lipid regulating agent, a muscle relaxant, a parasympathomimetic, a parathyroid calcitonin, a biphosphonate, a prostaglandin, a radio-pharmaceutical, a hormone, a sex hormone, an anti-allergic agent, an appetite stimulant, an anoretic, a steroid, a sympathomimetic, a thyroid agent, a vaccine, a vasodilator and a xanthine.

Exemplary types of small molecule drugs include, but are not limited to, acetaminophen, clarithromycin, azithromycin, ibuprofen, fluticasone propionate, salmeterol, pazopanib HCl, palbociclib, and amoxicillin potassium clavulanate.

Pharmaceutically Acceptable Excipients, Diluents, and Carriers

Pharmaceutically acceptable excipients include, but are not limited to:

(1) surfactants and polymers including: polyethylene glycol (PEG), polyvinylpyrrolidone (PVP), sodium lauryl sulfate, polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, carbomer and their polymers, emulsifiers, sugar gum, starch, organic acids and their salts, vinyl pyrrolidone and vinyl acetate;

(2) binding agents such as cellulose, cross-linked polyvinylpyrrolidone, microcrystalline cellulose;

(3) filling agents such as lactose monohydrate, lactose anhydrous, microcrystalline cellulose and various starches;

(4) lubricating agents such as agents that act on the flowability of a powder to be compressed, including colloidal silicon dioxide, talc, stearic acid, magnesium stearate, calcium stearate, silica gel;

(5) sweeteners such as any natural or artificial sweetener including sucrose, xylitol, sodium saccharin, cyclamate, aspartame, and acesulfame K;

(6) flavoring agents;

(7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride;

(8) buffers;

(9) Diluents such as pharmaceutically acceptable inert fillers, such as microcrystalline cellulose, lactose, dibasic calcium phosphate, saccharides, and/or mixtures of any of the foregoing;

(10) wetting agents such as corn starch, potato starch, maize starch, and modified starches, and mixtures thereof;

(11) disintegrants; such as croscarmellose sodium, crospovidone, sodium starch glycolate; and

(12) effervescent agents such as effervescent couples such as an organic acid (e.g., citric, tartaric, malic, fumaric, adipic, succinic, and alginic acids and anhydrides and acid salts), or a carbonate (e.g., sodium carbonate, potassium carbonate, magnesium carbonate, sodium glycine carbonate, L-lysine carbonate, and arginine carbonate) or bicarbonate (e.g. sodium bicarbonate or potassium bicarbonate)

Metal Oxide Material

The term "metal oxide material," in its broadest sense includes all materials formed from the reaction of elements considered metals with oxygen-based oxidants. Exemplary metal oxide materials include, but are not limited to, aluminum oxide, titanium dioxide, iron oxide, gallium oxide, magnesium oxide, zinc oxide, niobium oxide, hafnium oxide, tantalum oxide, lanthanum oxide, and zirconium dioxide. Exemplary oxidants include, but are not limited to, water, ozone, and inorganic peroxide.

Atomic Layer Deposition (ALD)

Atomic layer deposition is a thin film deposition technique in which the sequential addition of self-limiting monolayers of an element or compound allows deposition of a film with thickness and uniformity controlled to the level of an atomic or molecular monolayer. Self-limited means that only a single atomic layer is formed at a time, and a subsequent process step is required to regenerate the surface and allow further deposition.

Molecular Layer Deposition (MLD)

Molecular layer deposition is analogous to atomic layer deposition but using organic precursors and forming organic thin films. During a typical MLD process two homo-bifunctional precursors are used. A first precursor is introduced into a chamber. The molecules of the first precursor react with reactive groups on the substrate surface via the corresponding linking chemistry to add a molecular layer of the first precursor on the substrate surface with new reactive sites. After purging, a second precursor is introduced and the molecules of the second precursor react with the new reactive sites provided by the first precursor generating a molecular layer of the first precursor linked to the second precursor. This is followed by another purge cycle.

Reactor System

Figure 2:
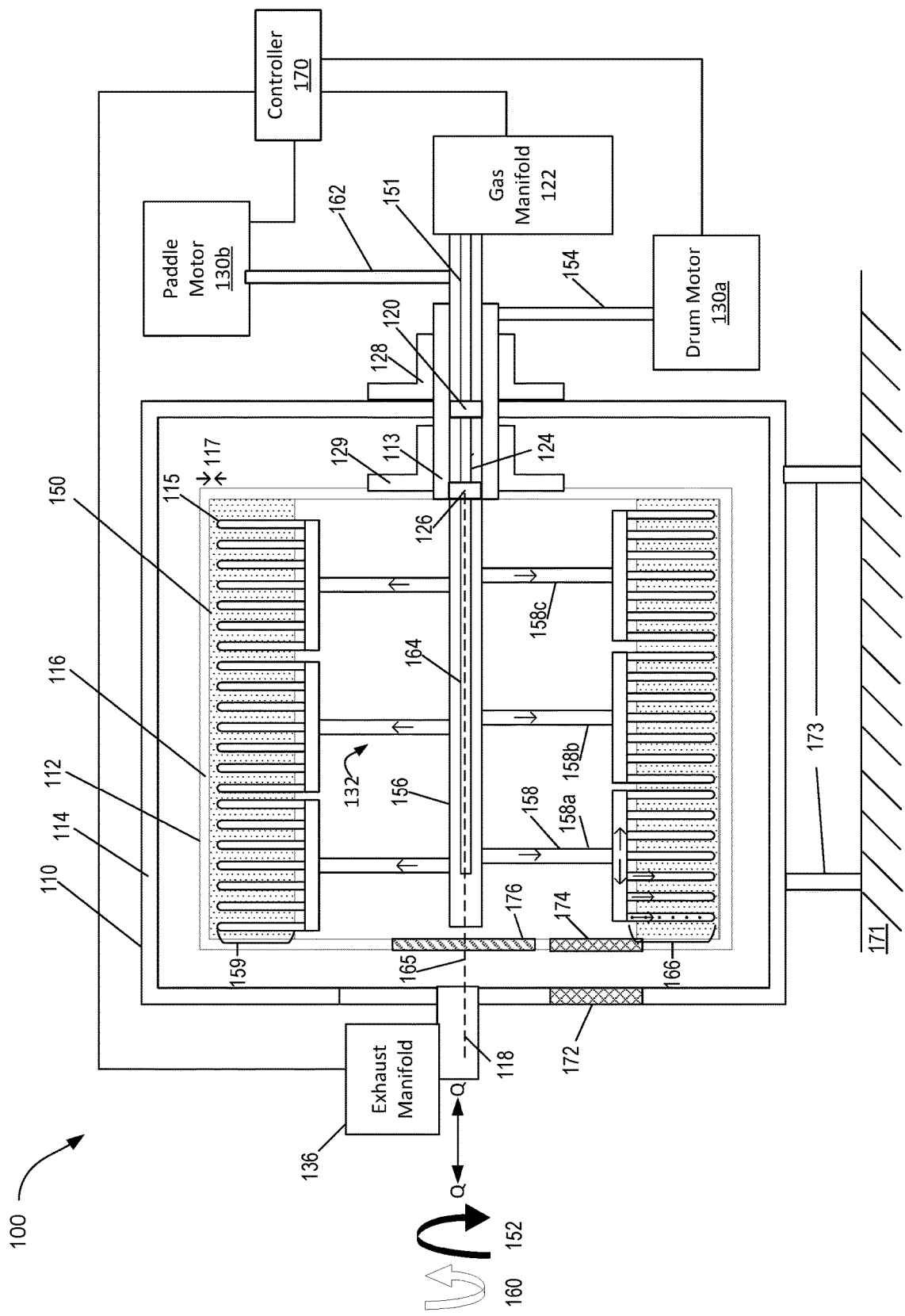
FIG. 2 is a schematic side view of the reactor of FIG. 1.

FIGS. 1-2 illustrate a reactor system 100 for coating particles with a thin-film coating. The reactor system 100 can perform the coating using ALD and/or MLD coating conditions. The reactor system 100 permits a deposition process (ALD or MLD), to be performed at higher (above 50° C., e.g., 50-100° C.) or lower processing temperature, e.g., below 50° C., e.g., at or below 35° C. For example, the reactor system 100 can form thin-film metal oxides on the particles primarily by ALD at temperatures of 22-35° C., e.g., 25-35° C., 25-30° C., or 30-35° C. In general, the particles can remain or be maintained at such temperatures. This can be achieved by having the reactant gases and/or the interior surfaces of the reactor chamber remain or be maintained at such temperatures. For example, heating can be achieved by a heater cartridge embedded in chamber body, by water channel in chamber body with use of heat exchanger, or by a heater jacket on the chamber body.

The reactor system 100 includes a stationary vacuum chamber 110 that encloses a rotary vacuum chamber 112. The stationary vacuum chamber 110 is enclosed by outer chamber walls 114. The rotary vacuum chamber 112 is enclosed by inner chamber walls 116. The chamber walls 114 and 116 can be a material, e.g., stainless steel, that is inert to the deposition process, and/or the interior surfaces of the chamber walls 114 and 116 can be coated with a material that is inert to the deposition process.

A cross-section of the rotary vacuum chamber 112 (e.g., as viewed along the central axis of the cylinder) of the rotary vacuum chamber can be uniform along the length of the chamber 112 (the length is along the central axis of the cylinder). This can help ensure uniform gas flow along the length of the chamber.

The stationary vacuum chamber 110 can include one or more vacuum ports 118 for exhausting gas, e.g., process gas, from the stationary chamber 110 and rotary vacuum chamber 112. The stationary vacuum chamber includes a gas inlet port 120 coupled to a chemical delivery system 122 located outside of the stationary vacuum chamber 110. The gas inlet port 120 further couples process gas via a gas delivery manifold 124 from the gas inlet port 120 located at the stationary vacuum chamber to a gas inlet port 126 located on a central axis 165 of the rotary vacuum chamber 112. The gas delivery manifold 124 is depicted schematically in FIG. 1 as entering the chamber from along the perimeter of the cylindrical chamber, however, in the embodiment described with reference to FIGS. 1 and 2, the gas delivery manifold is in-line with the central axis of the chamber 112 through a passage within the drive shaft 156 (e.g., as depicted in FIG. 2).

System 100 includes one or more motors 130a, 130b outside of the stationary vacuum chamber 110 that are configured to provide torque that translates into rotary motion of one or more components of the system 100. Motors 130a, 130b can be, for example, a drum motor 130a and a paddle motor 130b. Motors 130a and 130b can be, for example, brushless direct current (DC) DC motors. In some implementations, motors 130a and 130b have gear reduction built in, e.g., at a ratio of 20:1.

The drum motor 130a is coupled to the rotary vacuum chamber 112 and configured to provide torque that is translated into rotary motion of the rotary vacuum chamber 112 during operation of system 100. The paddle motor 130b is coupled to a paddle assembly 132 and configured to provide torque that is translated into rotary motion of the paddle assembly during operation of system 100. Though described with reference to FIGS. 1 and 2 as a drum motor 130a and a paddle motor 130b, fewer or more motors can be configured to provide torque that translates into rotary motion of the one or more components of the system 100.

System 100 includes a vacuum source 134 (e.g., one or more vacuum pumps) coupled to vacuum port 118 via a gas exhaust manifold 136. In some implementations, a gas source 139 is coupled to the gas exhaust manifold 136, e.g., a purge gas to dilute process gas that is exhausted from the system 100. Gas exhaust manifold 136 is configured to establish vacuum within the stationary vacuum chamber 110 and rotary vacuum chamber 112. The vacuum source 134 can be an industrial vacuum pump sufficient to establish pressures less than 1 Torr, e.g., 1 to 100 mTorr, e.g., 50 mTorr. The vacuum source 134 permits the chambers 110, 112 to be maintained at a desired pressure, and permits removal of reaction byproducts and unreacted process gases.

The chemical delivery system 122 includes multiple fluid sources 138 coupled by respective delivery tubes 140, controllable valves 142, and a fluid supply line 144. The chemical delivery system 122 delivers fluid to the gas delivery manifold 124 that inject the fluid in a vapor form into the rotary vacuum chamber 112 via the gas inlet port 126. The gas inlet port 126 is further coupled to a paddle manifold 164 which is coupled to one or more gas outlets 166 (as depicted in FIG. 2) that are located on at least one paddle 158 of the paddle assembly 132. The chemical delivery system 122 can include a combination of restrictors, gas flow controllers, pressure transducers, and thermal mass flow controllers/meters to provide controllable flow rate of the various gasses into the rotary vacuum chamber 112. The chemical delivery system 122 can also include one or more temperature control components, e.g., a heat exchanger, resistive heater, etc., to heat or cool the various gasses before they flow into the chamber 112.

The chemical delivery system 122 can include five fluid sources 138a, 138b, 138c, 138d, 138e. Two of the fluid sources, e.g., fluid sources 138a, 138b, can provide the two chemically different precursors or reactants for the deposition process for forming a metal oxide layer on the particles. For example, the first fluid source 138a can provide trimethylaluminum (TMA) or titanium tetrachloride (TiCl4), whereas the fluid gas source 138b can provide water.

Another two of the fluid sources, e.g., fluid sources 138c, 138d, can provide the two chemically different precursors or reactants for the deposition process for forming a polymer material on the metal oxide layer. For example, the third fluid source 138c can provide adipoyl chloride, and the fourth gas source 138d can provide ethylene diamine. One of the fluid sources, e.g., the fifth fluid source 138e, can provide an inert gas, e.g., argon or $N_2$, for purging between cycles or half-cycles in the deposition process.

Although FIG. 1 illustrates five fluid sources, the use of fewer gas sources could still be compatible with deposition of a metal oxide or polymer layer, and use of more gas sources could enable formation of an even wider variety of laminate structures.

For one or more of the fluid sources, the chemical delivery system 122 delivers the precursor or reactant in liquid form to the gas delivery manifold 124. The chemical delivery system 122 can include a vaporizer 146 to convert the liquid to vapor immediately before the precursor or reactant enters a gas inlet 120. This reduces upstream pressure loss to enable more pressure loss to occur across the particles 148 within the chamber 112. The more pressure loss that occurs across the particles 148, the lower the injection apertures can be place, and the more likely that all of the precursor will be reacted as it traverses the particle bed for a given flow rate. The vaporizer 146 can be immediately adjacent the outer wall of the stationary vacuum chamber 110, e.g., secured to or housed adjacent to the gas inlet port 120.

As shown in FIG. 1, gas delivery manifold 124 can be utilized to supply multiple precursor or reactant fluid sources 138. Manifold 151 is fluidically connected to gas inlet port 120.

The rotary vacuum chamber 112 is encapsulated within and supported by the stationary vacuum chamber 110. The rotary vacuum chamber 112 includes an inner surface 150 along an inner diameter of the chamber walls 116. In some implementations, as depicted in FIGS. 1 and 2, the rotary vacuum chamber includes a cylindrical portion, where an axis of rotation is aligned on a center axis of the cylinder. The rotary vacuum chamber 112 is connected to a vacuum tight rotary union, and is connected to the stationary vacuum chamber 110 by screws inside the rotary vacuum chamber 112 via the rotary motion feedthrough 129, as depicted in FIG. 2.

Referring now to FIG. 2, the rotary vacuum chamber 112 is coupled to one or more motors, e.g., drum motor 130a, where the drum motor 130a is operable to generate torque that can translate into rotary motion of the rotary vacuum chamber in a first direction 152 (e.g., clockwise with respect to an axial axis Q-Q. The coupling between the rotary vacuum chamber 112 and the one or more motors can be through a rotary motion vacuum feedthrough 128, as depicted in FIG. 2. One or more mechanical couplings 154 can be utilized between the drum motor 130a and the rotary vacuum chamber 112 to translate a torque output from the motor 130a into a rotary motion in the first direction 152 of the rotary vacuum chamber 112. In some implementations, mechanical couplings 154 can be a belt and pulley system, where a belt can have compliance to allow for some misalignment and run out of the drum motor 130a and the rotary vacuum chamber 112. Motion of the rotary vacuum chamber 112 can be clockwise (CW), counter-clockwise (CCW), or can alternate between CW and CCW. In some implementations, port 113 of the rotary vacuum chamber is coupled to the rotary motion feedthrough 129 by a key block to transfer torque between the drum motor 130a and the rotary vacuum chamber 112.

Paddle assembly 132 includes a drive shaft 156 and one or more paddles 158 coupled to the drive shaft 156. Drive shaft 156 is oriented along an axial axis Q-Q of the rotary vacuum chamber 112. Paddles 158 are affixed to the drive shaft 156 along the length of the drive shaft 156. The paddles are positioned such that an outer surface 115 of the paddles 158 is spaced by a threshold distance, e.g., a gap 117, from the inner surface 150 of the rotary vacuum chamber 112. Details of the paddles 158 are discussed below.

The paddle assembly 132 is coupled to one or more motors outside the vacuum chamber 110, e.g., paddle motor 130b, via the rotary vacuum feedthrough 128 (e.g., including vacuum-compatible bearings). The paddle motor 130b is configured to apply torque to the drive shaft 156 such that the drive shaft 156 rotates about a center axial 118 axis aligned with axis Q-Q of the drive shaft 156 in a second direction 160. One or more mechanical couplings 162 can be utilized between the paddle motor 130b and the drive shaft 156 to translate a torque output from the motor 130b into a rotary motion in the second direction 160 (e.g., counter clockwise with respect to the axial axis Q-Q) of the paddle assembly 132. In some implementations, mechanical couplings 162 can be a belt and pulley system, where a belt can have compliance to allow for some misalignment and run out of the paddle motor 130b and the drive shaft 156 of the paddle assembly 132. Motion of the drive shaft 156 can be clockwise (CW) or counter-clockwise (CCW).

In some implementations, the rotary motion vacuum feedthrough 128 is a bearing vacuum seal that can be used to seal the stationary vacuum chamber 110 from the external environment. The drive shaft 156 can then pass through a portion of the stationary vacuum chamber 110 and through a port 113 of the rotary vacuum chamber 112 such that the drive shaft 156 to rotate freely with respect to the rotary vacuum chamber 112. A lip seal can be located between the port 113 and the rotary motion feedthrough 129 to prevent powder in the rotary vacuum chamber 112 from traveling down the drive shaft 156 to the bearings of the rotary motion feedthrough 129.

In some implementations, the first direction 152 and the second direction 160 are opposite directions, e.g., clockwise and counter-clockwise. The first direction 152 and second direction 160 can instead be in a same direction, e.g., both clockwise or both counter-clockwise.

Paddle assembly 132 further includes a paddle manifold 164 that is coupled to the gas inlet port 126. The paddle manifold 164 connects the inlet port 126 to one or more gas outlets 166 located on at least one paddle 158 of the paddle assembly 132. This permits the process gas (e.g., reactant or precursor gas) to flow from the chemical distribution system 122 and be injected into the rotary vacuum chamber 112 via the outlets on the paddle 158. In some implementations, multiple paddles 158a, 158b, 158c of the paddle assemble 132 each include multiple gas outlets 166 coupled to the paddle manifold 164 such that process gas is injected into the rotary vacuum chamber via the multiple gas outlets 166.

The multiple paddles 158 of the paddle assembly 132 can be distributed along the axial axis of the drive shaft 156, e.g., spaced at uniform intervals, to ensure an even distribution of process gas injected into the rotary vacuum chamber 112 via the gas outlets 166 located on each of the multiple paddles 158.

As depicted in FIG. 2 the paddles 158 of the paddle assembly 132 are oriented on the drive shaft 156 such that the alignment of the paddles results in little or no lateral gaps of interaction between the paddles 158 and the particles 148. In some implementations, as depicted in FIG. 2, only the portion 159 of the paddles 158 of the paddle assembly 132 are in contact with the particles 148 during the operation of the system 100.

In some implementations, process gas is injected into the rotary vacuum chamber 112 from the gas outlets located on the paddles 158 in a direction 168 opposite an instantaneous motion of the paddles 158 due to rotation of the paddle assembly 132 in the second direction 160. In other words, the multiple gas outlets 166 are located on a trailing edge of the paddles 158 such that process gas is injected into the rotary vacuum chamber 112 from the gas outlets 166 in a direction that is opposite the rotary motion of the paddles 158. In one example, the paddle assembly 132 is rotating in a clockwise direction and the process gas is injected into the rotary vacuum chamber 112 in a counter-clockwise direction. Further details of the configuration of the gas outlets are discussed below.

An inert carrier gas, e.g., $N_2$, can flow from one of the fluid sources, e.g., the fluid source 138e, into the paddle manifold 164. In operation, the carrier gas can flow continuously into the paddle manifold 164, i.e., whether or not the precursor or reactor gas is flowing into the paddle manifold 164. When the precursor or reactor gas is not being injected into the chamber 112 through the manifold 164, the flow of the carrier gas can prevent backstreaming into the gas outlets 166 of the another precursor or reactor gas that is being injected from another manifold. The flow of carrier gas can also prevent fouling of the gas outlets 166, e.g., blockage of the aperture, by the particles 148. In addition, the carrier gas can provide the purge gas for the purge operation when the precursor or reactor gas is not being injected into the chamber 112.

The flow of carrier gas into the vaporizer 146 when the precursor gas is also flowing can improve vaporization of the precursor or reactant liquid. Without being limited by any particular theory, the carrier gas flow can assist in shearing the liquid during aerosolization, which can lead to smaller droplet size, which can be vaporized more quickly. Flow of the carrier gas into the paddle manifold 164 when the precursor gas is also flowing can assist in drawing precursor gas out of the vaporizer 146.

In some implementations, one or more temperature control components are integrated into the inner chamber walls 116 to permit control of the temperature of the rotary vacuum chamber 112. For example, resistive heater, a thermoelectric cooler, a heat exchanger, or coolant flowing in cooling channels in the chamber wall, or other component in or on the side walls 116.

System 100 further includes a controller 170 that is operable to control the actions of at least the chemical distribution system 122 and the one or more motors 130a, 130b. Controller 170 can be configured to operate the paddle motor 130b to generate a rotary motion of the paddle assembly 132 in the second direction 160 at rotational speeds up to 200 rotations per minute (rpm). Controller 170 can be further configured to operate the drum motor 130a to generate a rotary motion of the rotary vacuum chamber 112 in the first direction 152 at rotational speeds up to 200 rpm, for example, ranging between 1-60 (rpm). In some implementations, the controller 170 is configured to operate the drum motor 130a to produce a rotational speed of the rotary vacuum chamber 112 that exceeds a threshold rotational motion, e.g., that is greater than 15 rpm. As depicted in FIGS. 1 and 2, the rotation rate is sufficiently high that particles 148 are centrifugally forced against the inner surface 150 of the rotary vacuum chamber 112 (this can be referred to as "fast" rotary motion). This can result in a toroidal bed of particles 148 on the inner surface 150. An amount of compression of the bed of particles formed by the fast rotary motion of the rotary vacuum chamber 112 can depend, for example, of the rotational speed of the rotary vacuum chamber 112. The controller 170 can also be coupled to various sensors, e.g., pressure sensors, flow meters, etc., to provide closed loop control of the rotation rate of the chamber and the pressure of the gasses in the chamber 110.

In some implementations, rotational speed of the drum motor 130a can be selected based on a desired forced to be experienced by the particles 148 present within the rotary vacuum chamber 112 during operation of the reactor as described by equation (1)

$$F \propto a_i * r \qquad (1)$$

where F is a force experienced by the particles 148 that is proportional to the acceleration of the rotary vacuum chamber 112 (e.g., in rotations per minute-squared ($rpm^2$)) multiplied by a radius r of the rotary vacuum chamber 112. Above a threshold amount of force experienced by the particles 148, the particles 148 will be centrifugally forced against the inner surface 150 of the rotary vacuum chamber 112. An amount of force F depends in part on a radius of the rotary vacuum chamber 112 that can range, for example, between 100-300 mm. In one example, a radius of the rotary vacuum chamber 112 is 215 mm.

In general, the controller 170 is configured to operate the reactor system 100 in accord with a "recipe." The recipe specifies an operating value for each controllable element as a function of time. For example, the recipe can specify the times during which the vacuum source 132 is to operate, the times of and flow rate for each gas source 138a-138e, the rotation rate of the rotary vacuum chamber 112 and the drive shaft 156 as set by the motors 130a, 130b, etc. The controller 170 can receive the recipe as computer-readable data (e.g., that is stored on a non-transitory computer readable medium).

The system 100 further includes a first loading port 172 located on the stationary vacuum chamber 110 and a second loading port 174 located on the rotary vacuum chamber 112 which can be aligned to allow access to the inside of the rotary vacuum chamber 112 in order to load particles 148 to be processed. The first loading port 172 and second loading port 174 can be sealed during operation of the reactor system 100 such that the ports hold against vacuum established within the respective vacuum chambers. Methods for operation of the reactor system 100 are described in further detail below.

The system 100 further includes a particle filter 176 that allows to exhaust gas from the rotary vacuum chamber 112 via the vacuum port 118 located in the stationary vacuum chamber 110. In some implementations, as depicted in FIG. 2 the vacuum port 118 for the system 100 is in-line with the drive shaft 156 along the Q-Q axis. In addition, the system 100 can include a filter cleaner to clear particles off the filter 176. As one example, the filter cleaner can be a mechanical knocker to strike the filter; this make shake particles off the filter. As another example, gas source 139 can periodically provide a pulse of inert gas, e.g., nitrogen, into the exhaust manifold 136 between the vacuum port 118 and the vacuum source 134. The pulse of gas travels through the filter 176 back toward the chamber 112 and can blow the particles off of the filter 176. Isolation valves 139a, 139b can be used to ensure that only one of the gas source 138 or vacuum source 134 is fluidically coupled at a time to the exhaust manifold 136.

Figure 3A:
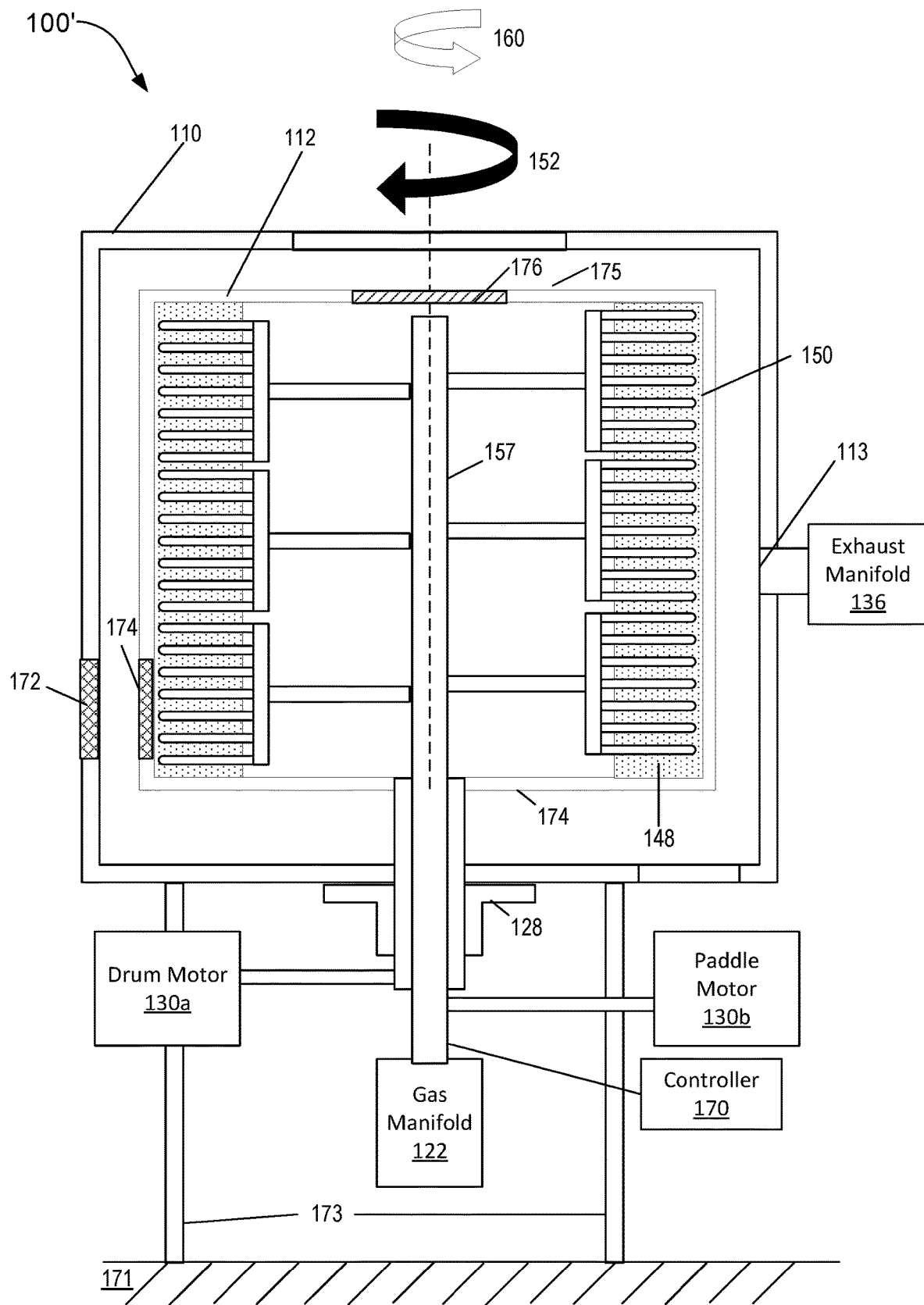
FIG. 3A is a schematic side view of another example reactor for ALD and/or CVD coating of particles, e.g., drugs, that includes a vertically-oriented rotary vacuum chamber.

The reactor system 100 can include a base 173 to support the reactor 100 on a mounting surface 171. In some implementations, the reactor system 100 is secured to the base 173 such that the axial axis 165 is perpendicular to the mounting surface 171. As a result, assuming a horizontal mounting surface 171, the drive shaft and axial axis 165 are parallel to gravity, i.e., are vertically oriented. FIG. 3A is a schematic side view of another example reactor for ALD and/or CVD coating of particles, e.g., drugs, that includes a vertically-oriented rotary vacuum chamber 100'.

In some embodiments, as depicted in FIGS. 1 and 2, the reactor system 100 is secured to the base 173 such that the axial axis 165 and the drive shaft 156 are perpendicular to the mounting surface 171. As a result, assuming a horizontal mounting surface, the axis of rotation of the rotary vacuum chamber 112 is perpendicular to gravity.

As depicted in FIG. 3A, the vertical drive shaft 157 is coupled to the vertically-oriented rotary vacuum chamber 135 at a bottom surface 174 of the rotary vacuum chamber 135. In some implementations, the vertical drive shaft 157 can instead by coupled to the vertically-oriented rotary vacuum chamber 135 at a surface 175 of the rotary vacuum chamber 135.

During operation of the reactor system 100' depicted in FIG. 3A, the controller 170 is configured to operate the drum motor 130a to produce rotational speed of the vertically-oriented rotary vacuum chamber 135 that is sufficiently high that particles 148 are centrifugally forced against the inner surface 150 of the vertically-oriented rotary vacuum chamber 135. This can result in a toroidal bed of particles 148 on the inner surface 150.

In some implementations, a vacuum port 119 for exhausting gas from the chamber 113 is located on a side of the stationary vacuum chamber 110. The vacuum port 119 can be oriented opposite the rotary motion vacuum feedthrough 128 that couples the drive shaft 157 to into the chamber 113.

Figure 3B:
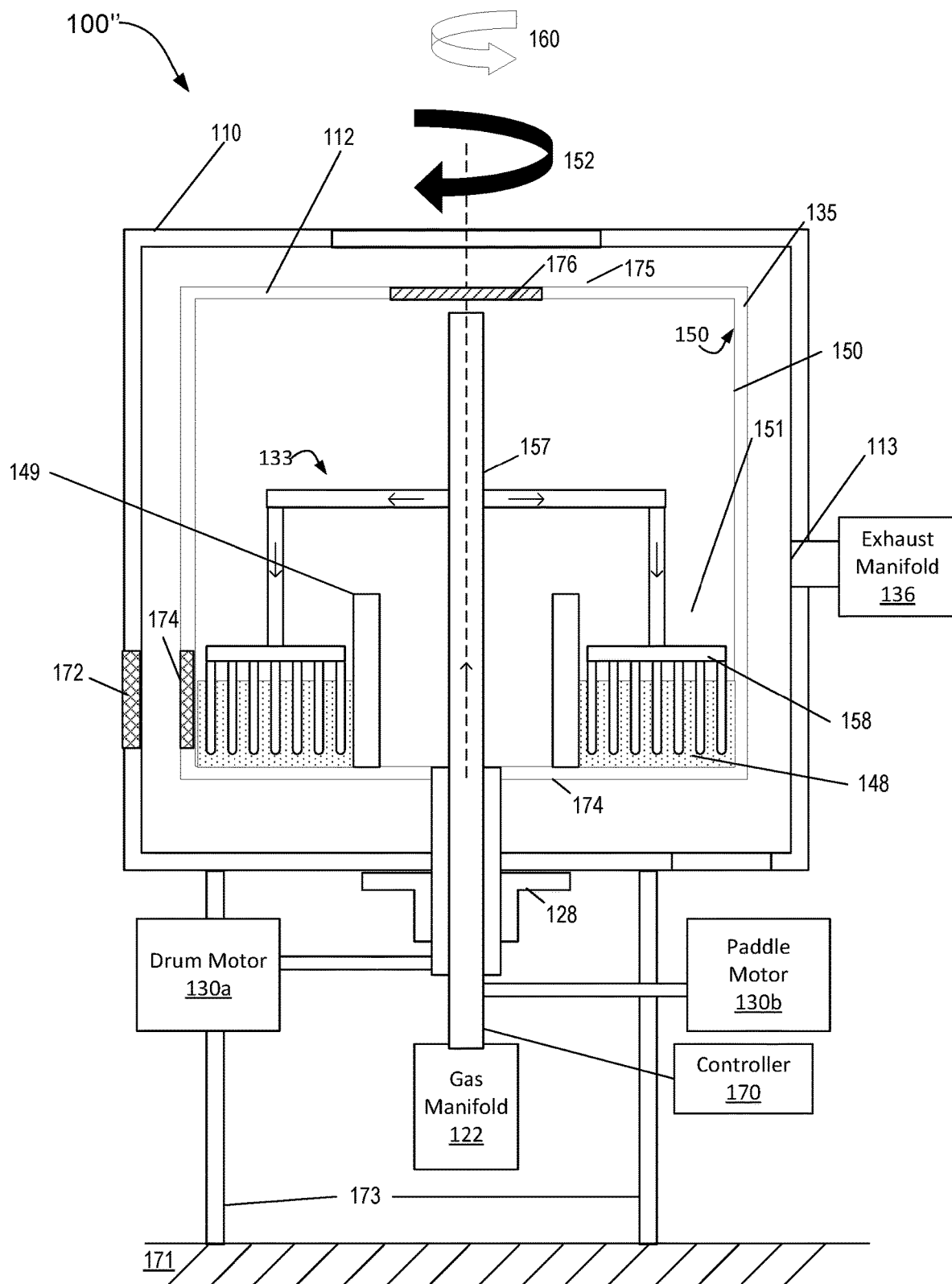
FIG. 3B is a schematic side view of another example reactor for ALD and/or CVD coating of particles, e.g., drugs, that includes a vertically-oriented rotary vacuum chamber.

FIG. 3B is a schematic side view of another example reactor for ALD and/or CVD coating of particles, e.g., drugs, that includes a vertically-oriented rotary vacuum chamber 100". As depicted in FIG. 3B, the vertical drive shaft 157 is coupled to the vertically-oriented rotary vacuum chamber 135 at a bottom surface 174 of the rotary vacuum chamber 135. In some implementations, the vertical drive shaft 157 can instead by coupled to the vertically-oriented rotary vacuum chamber 135 at a surface 175 of the rotary vacuum chamber 135.

Reactor 100" additionally includes an inner wall 149 (e.g., defining an inner circumference) within the rotary vacuum chamber 135, where the inner wall 149 separates a first region 151 of the rotary vacuum chamber that is configured to receive particles 148 from a second region 153 that is not configured to receive particles 148. Paddles 158 of the paddle assembly 133 are coupled to the drive shaft 157 such that the paddles 158 and at least one gas outlet 166 located on the paddles 158 are located partially within the first region 151. During operation of the reactor system 100' depicted in FIG. 3B, the controller 170 is configured to operate the drum motor 130a to produce rotational speed of the vertically-oriented rotary vacuum chamber 135 such that the particles within the chamber 135 do not form a toroid against the inner surface 150 of the rotary vacuum chamber 135.

Figure 4:
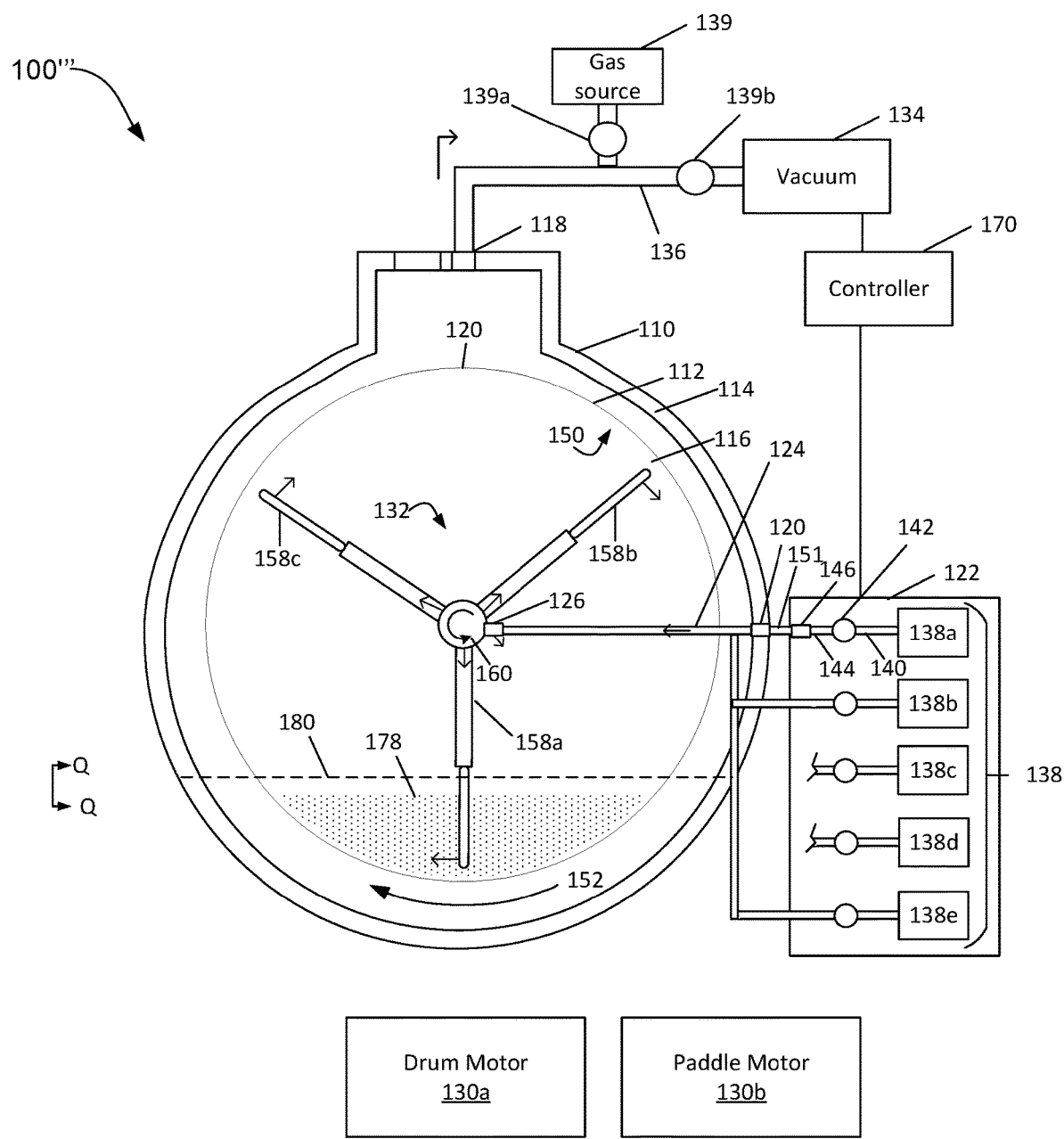
FIG. 4 is a schematic front view of another example reactor for ALD and/or CVD coating of particles, e.g., drugs, that includes a rotary vacuum chamber.
Figure 5:
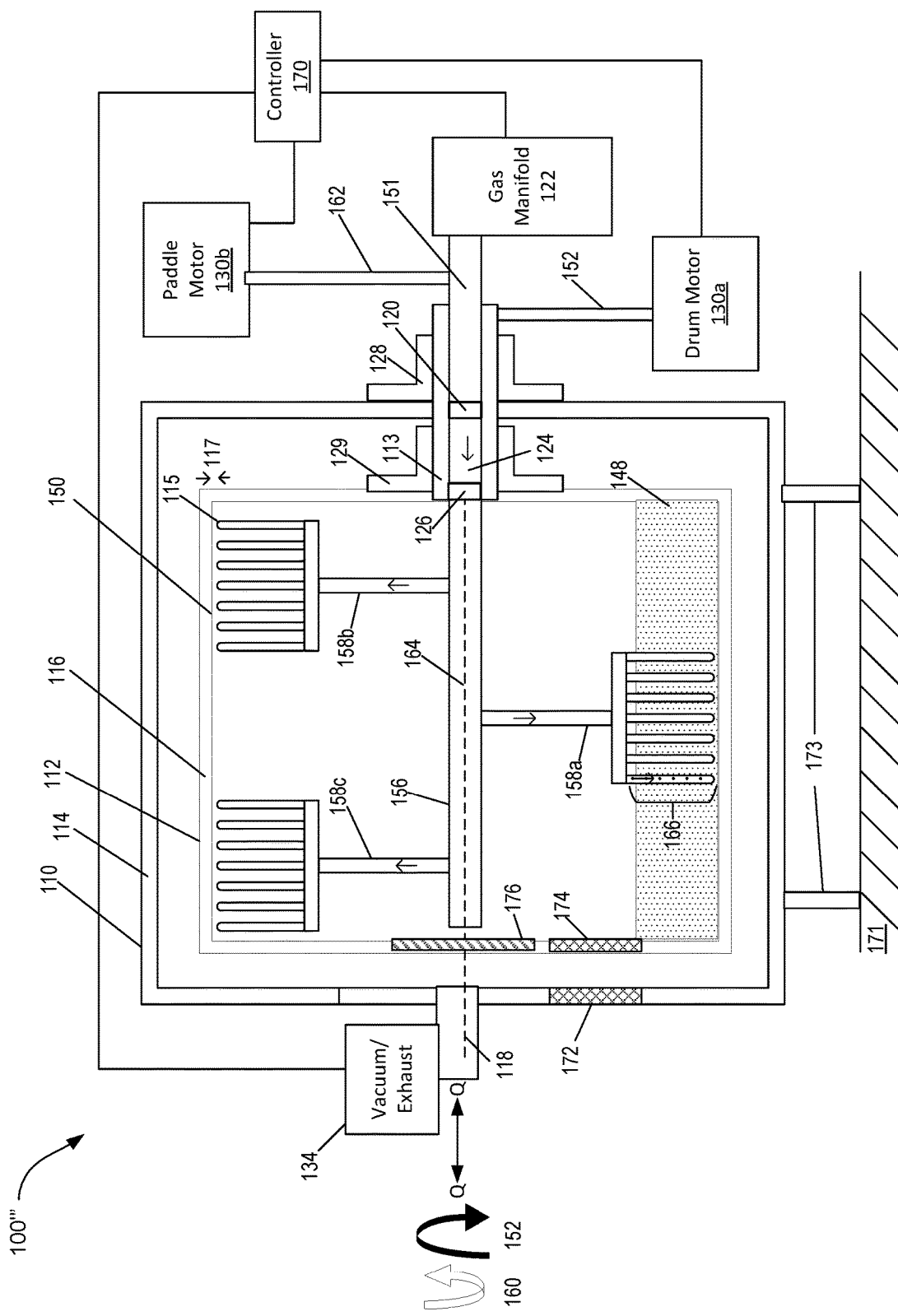
FIG. 5 is a schematic side view of the reactor of FIG. 4.

FIGS. 4-5 illustrate another example reactor system 100''' for coating particles with a thin-film coating. The reactor system 100''' can perform the coating using ALD and/or MLD coating conditions.

In some implementations, a rotational speed of the rotary vacuum chamber 112 is less than a threshold rotational speed, e.g., less than 15 rpm, such that particles 148 within the rotary vacuum chamber experience tumbling agitation while the rotary vacuum chamber 112 is in rotational motion. For example, the chamber 112 can rotate at 6-15 rpm. At sufficiently low rotation speeds, the particles within the chamber 112 do not form a toroid against the inner surface 150 of the rotary vacuum chamber 112. A controller 182 is configured to operate the drum motor 130a to produce rotational speed of the rotary vacuum chamber 112 in the first direction 152 that is less than the threshold rotational speed.

During operation of the reactor system 100''', particles loaded into the rotary vacuum chamber 112 form a particle bed 178 located below a lower portion 180 of the interior of the rotary vacuum chamber 112, relative to gravity. As the rotary vacuum chamber 112 rotates about the axial axis defined by Q-Q, the particles in the particle bed 178 undergo a tumbling agitation. Some portion of the particles may be temporarily elevated due to rotation, but fall back into the powder bed due to gravity. Thus, most or all of the particles remain in the lower portion 180 of the rotary vacuum chamber 112.

In some implementations, the rotary vacuum chamber 112 rotates at rotational speeds less than a threshold rotational speed, e.g., at a speed of 6-15 RPM. The controller 170 can be configured to operate the drum motor 130a to generate rotary motion in the rotary vacuum chamber 112 in alternating directions, e.g., alternating between clockwise and counter-clockwise rotary motion. This can assist in agitation of the particles to improve uniformity of the coating. A rate of alternating directions, e.g., an amount of time for which the chamber 112 is rotating in a first direction vs a second direction, can be selected based on the particular recipe and/or particles 178 that are being coated by the reactor system 100'''.

In some implementations, as depicted in FIGS. 4 and 5, one or more paddles 158 of the paddle assembly 132 are not in contact with the particle bed 178 at a given time during the rotation of the paddle assembly about the axial axis defined by Q-Q. For example, paddle 158a is in contact with the particle bed 178 and paddles 158b and 158c are not in contact with the particle bed 178 at an instant of the rotation of the paddle assembly 132.

In some implementations, as depicted in FIG. 4, the rotary vacuum chamber 112 rotates in a first direction 152 and the paddle assembly 132 rotates in a second, opposite direction 160. A center of rotation of each of the rotary vacuum chamber 112 and the paddle assembly 132 is a same axial axis aligned with a center of the cylindrical portion of the rotary vacuum chamber 112.

In some implementations, the rotary vacuum chamber 112 includes baffles on an inner surface 150 of the chamber 112, where the baffles can be oriented to move particles from the particle bed 178 from a first side of the rotary vacuum chamber 112 to a second side of the rotary vacuum chamber 112 as the rotary vacuum chamber 112 rotates about the axial axis at a rotational speed in the first direction 152.

As discussed above with reference to FIGS. 1 and 2, a paddle 158 of the paddle assembly 132 can have various configurations. Described here are three variations on the paddle design for the paddle assembly. However, alternative embodiments having similar functionality can be imagined. In general, shape and orientation of paddles 158 of the paddle assembly 132 are selected such that the paddles 158 of the paddle assembly 132 provide mechanical agitation of particles 148 (and/or particle bed 178) that are present within the rotary vacuum chamber 112 during operation of the reactor system (e.g., reactor systems 100, 100', 100'''). The paddles 158 further include one or more gas outlets 166 located on the paddles 158 to inject process gas from the chemical distribution system 122 into the rotary vacuum chamber 112 during operation of the reactor system 100, 100', 100'''. Paddles 158 are affixed on a drive shaft (e.g., drive shaft 156) and oriented along the drive shaft 156 to provide substantially even coverage of mechanical agitation and process gas injection along a length of the cylindrical portion of the rotary vacuum chamber 112 during operation of the reactor system 100, 100', 100''' (e.g., during rotational motion of the paddle assembly 132 in the second direction 160).

Figure 6A:
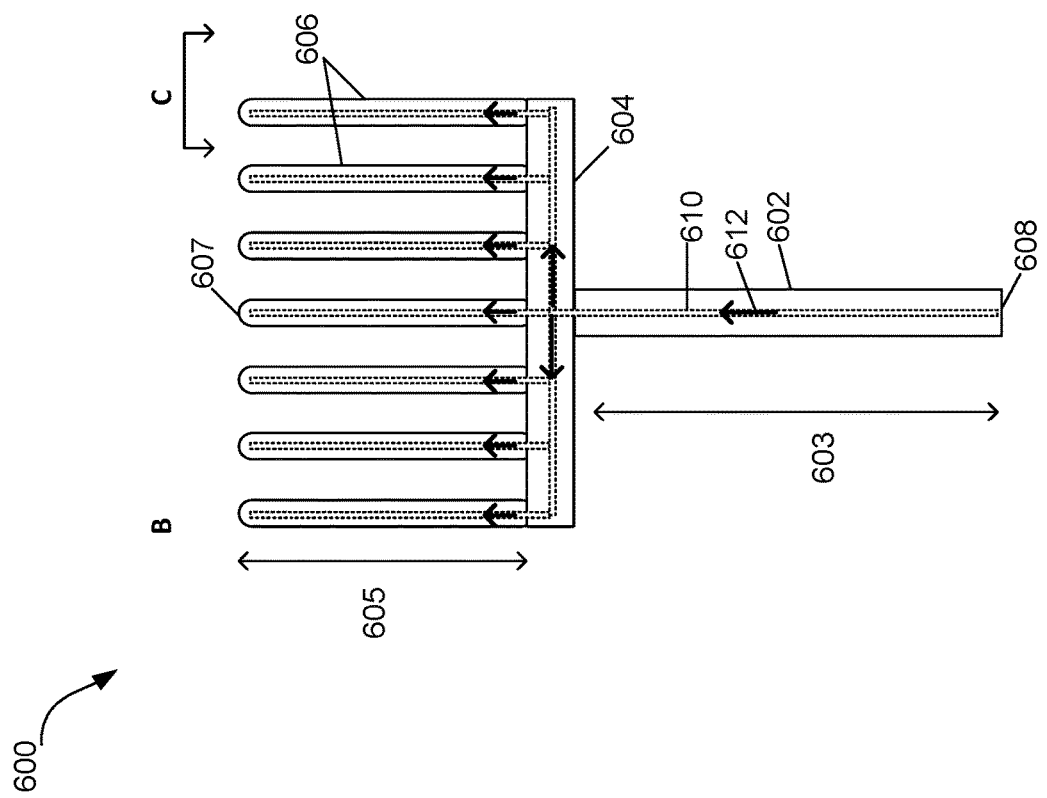
FIGS. 6A-6C are schematics of various views of a rake-shaped paddle.
Figure 6C:
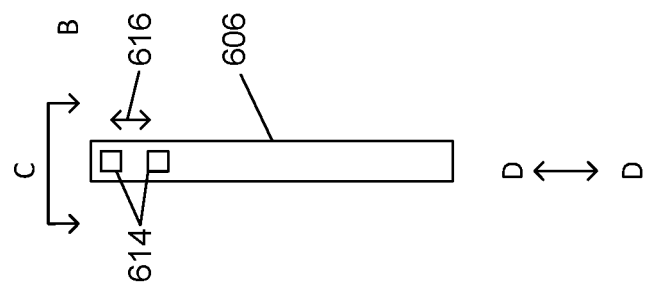
Figure 6B:
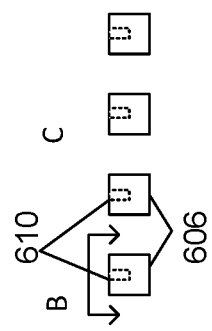

As depicted in FIGS. 1-5, a paddle 158 of the paddle assembly 132 can be a rake-shaped paddle. FIGS. 6A-6C are schematics of various views of a rake-shaped paddle 600. As depicted in FIG. 6A, rake-shaped paddle 600 includes a base shaft 602 that is coupled to a drive shaft of the paddle assembly (e.g., drive shaft 156 of the paddle assembly 132). The paddle further includes a cross-bar 604 coupled to the base shaft 602 of the paddle 600, and multiple tines 606 each coupled to the cross-bar 604 and extending away from the base 608 of the paddle 600. The multiple tines 606 can have length ranging 50-100 mm, e.g., 78 mm. A profile of the tines 606 can be selected such that the tines 606 move gently through the powder as the paddle assembly rotates. In one example, the tines 606 are tear-drop shaped.

In some implementations, dimensions of the paddle 600 e.g., a length of the base shaft 603 and a length 605 of the tines 606, can be selected such that a distance (e.g., gap 117) between an outer surface 607 (e.g., the outer surface 115) of the tines 606 of the paddle 600 is less than a threshold distance (e.g., 1-3 mm) from an inner surface of the rotary vacuum chamber (e.g., rotary vacuum chamber 112) when the paddle 600 is affixed to the drive shaft of the paddle assembly (e.g., drive shaft 156 of paddle assembly 132).

Each of the base shaft 602, cross-bar 604, and multiple tines 606 has internal tubing and/or passageways 610 that are coupled to the paddle manifold (e.g., paddle manifold 164). Process gas can flow 612 through the base shaft 602, into the cross-bar 604 and further into the multiple tines 606 via the internal tubing and/or passageways 610. FIG. 6B depicts a "top-down" view C indicating an example location of the internal tubing and/or passageways 610 within the tines 606 of the paddle 600.

As depicted in FIG. 6C, the process gas is then injected into the rotary vacuum chamber (e.g., rotary vacuum chamber 112) via multiple gas outlets 614 (e.g., gas outlets 166) located on the paddle 600, e.g., one or more gas outlet 614 located on each tine 606. Gas outlets 614 can have a diameter ranging 0.5-3 mm, e.g., 1 mm in diameter with a spacing between adjacent gas outlets 614 ranging between 5-15 mm, e.g., 8 mm spacing. A number of gas outlets 614 per tine 606 can range between 5-20 gas outlets 614, e.g., 7 gas outlets 614 per tine 606. The gas outlets 614 can be arranges on the tine 606 along a line that bisects a width of the tine 606.

In some implementations, the multiple gas outlets 614 are located on the multiple tines 606 of the paddle 600. For example, each tine 606 can have a single gas outlet 614. The multiple gas outlets 614 are located on a surface indicated by B of each tine 606, corresponding to a trailing edge of the paddle 600 when the paddle 600 is rotating about the second direction (e.g., second direction 160) within the rotary vacuum chamber 112. Though depicted in FIG. 6C as multiple gas outlets 614 aligned along an axis D-D with evenly distributed spacing 616 between each gas outlet 614, the multiple gas outlets can be off-set with respect to each other and/or can have variable spacing.

Figure 6D:
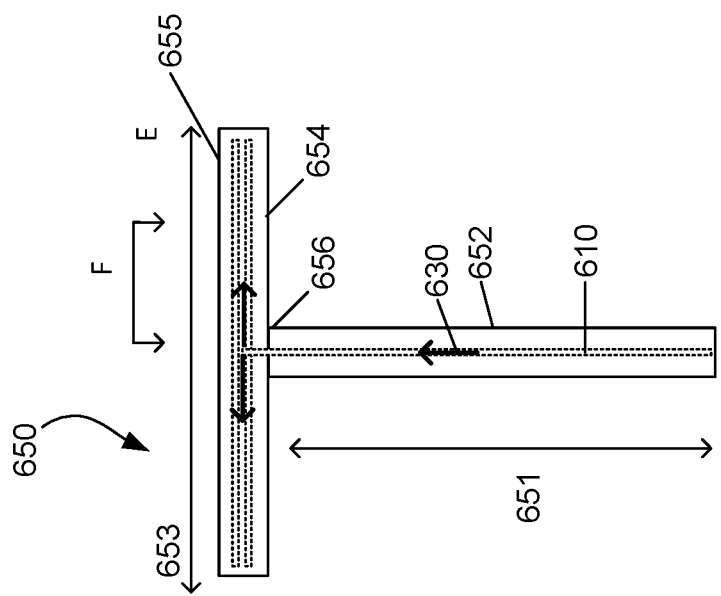
FIGS. 6D-6G are schematics of various views of a T-shaped paddle with and without an anti-static brush component.

In some implementations, a paddle of the paddle assembly (e.g., paddle assembly 132) is T-shaped. FIGS. 6D-6G are schematics of various views of T-shaped paddle 650 with and without an anti-static brush component 664. As depicted in FIG. 6D, T-shaped paddle 650 includes a base shaft 652 and a cross-bar 654, where the base shaft 652 is coupled to the drive shaft of the paddle assembly (e.g., drive shaft 156 of paddle assembly 132), and the cross-bar 654 is located on an end 656 of the base shaft 652 opposite of a surface where the base shaft 652 is coupled to the drive shaft.

In some implementations, dimensions of the paddle 650 e.g., a length 651 of the base shaft 652 and a width 653 of the cross-bar 654, can be selected such that a distance (e.g., gap 117) between a surface 655 (e.g., surface 115) of the cross-bar 654 are less than a threshold distance (e.g., 1-3 mm) from an inner surface of the rotary vacuum chamber (e.g., rotary vacuum chamber 112) when the paddle 650 is affixed to the drive shaft of the paddle assembly (e.g., drive shaft 156 of paddle assembly 132).

Each of the base shaft 652 and the cross-bar 654 has internal tubing and/or passageways 610 that are coupled to the paddle manifold (e.g., paddle manifold 164). Process gas can flow 630 through the base shaft 652 and into the cross-bar 654 via the internal tubing and/or passageways 610. FIG. 6E depicts a "top-down" view C indicating an example location of the internal tubing and/or passageways 610 within the cross-bar 654 of the paddle 650.

Figure 6F:
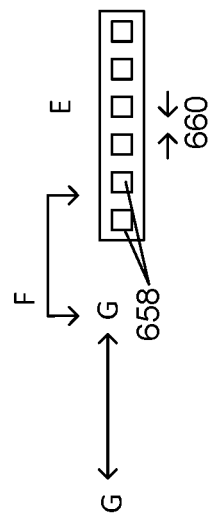
Figure 6E:
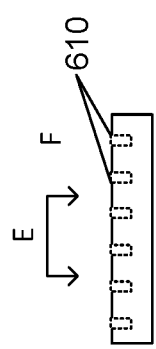

As depicted in FIG. 6F, the process gas is then injected into the rotary vacuum chamber (e.g., rotary vacuum chamber 112) via multiple gas outlets 658 (e.g., gas outlets 166) located on the paddle 650, e.g., one or more gas outlet 658 located on each cross-bar 654. Gas outlets 658 can have a diameter ranging 0.5 mm-3 mm, e.g., 1 mm diameter with a spacing between gas outlets 658 ranging between 5-15 mm, e.g., 10 mm between each gas outlet 658. A number of gas outlets 658 located on each paddle 650 can range between 5-20 gas outlets 658, e.g., 8 gas outlets In some implementations, the multiple gas outlets 658 are located on the cross-bar 654 of the paddle 650, where the multiple gas outlets 658 are located on a surface indicated by E of the cross-bar 654, corresponding to a trailing edge of the paddle 650 when the paddle 650 is rotating about the second direction (e.g., second direction 160) within the rotary vacuum chamber 112. Further detail of a paddle assembly including T-shaped paddles 650 are discussed below with reference to FIGS. 7A, 7B.

Though depicted in FIG. 6F as multiple gas outlets 654 aligned along an axis G-G with evenly distributed spacing 660 between each gas outlet 658, the multiple gas outlets can be off-set with respect to each other and/or can have variable spacing. The multiple gas outlets 658 can be distributed on the trailing edge of the paddle 650 in multiple rows and/or in multiple patterns on the surface of the trailing edge surface of the cross-bar indicated by E, where a configuration of the multiple gas outlets 658 can be selected to optimize an substantially even distribution of process gas injected into the rotary vacuum chamber by the paddle assembly (e.g., rotary vacuum chamber 112 by paddle assembly 132).

Figure 6G:
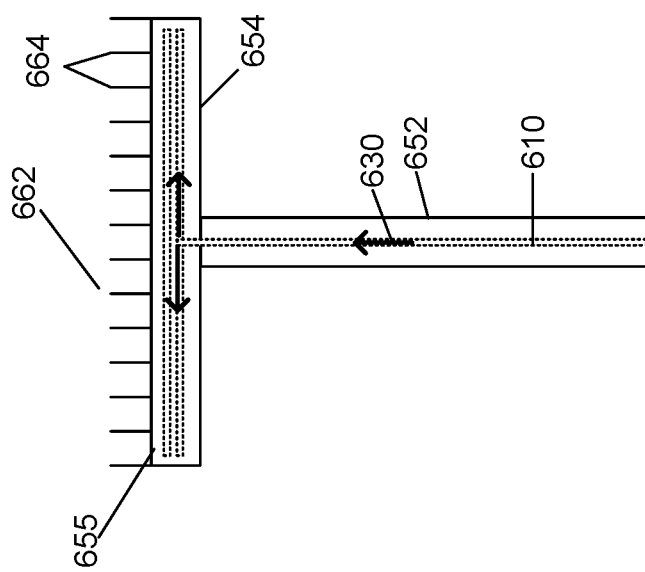

In some implementations, the T-shaped paddle 650 further includes an anti-static brush component 662 located on the outer surface 655 of the cross-bar 654, as depicted in FIG. 6G. The anti-static brush component 662 can be composed of a semi-flexible material (e.g., a high-temperature inert rubber/plastic, thin aluminum fins, or the like). A material of the anti-static brush component 662 can be selected to contact the inner surface of the rotary vacuum chamber in order to sweep particles (e.g., particles 148 and/or particle bed 178) from the inner surface of the rotary vacuum chamber during the rotary motion of the paddle assembly. The material of the anti-static brush component 662 can further be selected to avoid damaging the inner surface of the rotary vacuum chamber (e.g., avoid scratching or denting the surface) due to the contact between the anti-static brush component 662 and the inner surface of the rotary vacuum chamber 112.

The anti-static brush component 662 is located between the end surface 655 of the T-shaped paddle 650 and in contact with the inner surface of the rotary vacuum chamber (e.g., inner surface 150 of the rotary vacuum chamber 112) when the paddle 650 is affixed and oriented on the drive shaft of the paddle assembly within the rotary vacuum chamber (e.g., drive shaft 156 of paddle assembly 132 in rotary vacuum chamber 112).

In some implementations, the anti-static brush component 662 includes multiple fins 664, where a density and/or spacing of the fins 664 of the anti-static brush component 662 can be selected to ensure coverage of an entire length of the inner surface of the rotary vacuum chamber through a complete rotation of the paddle assembly (e.g., 360 degrees) with respect to the rotary vacuum chamber.

Figure 7A:
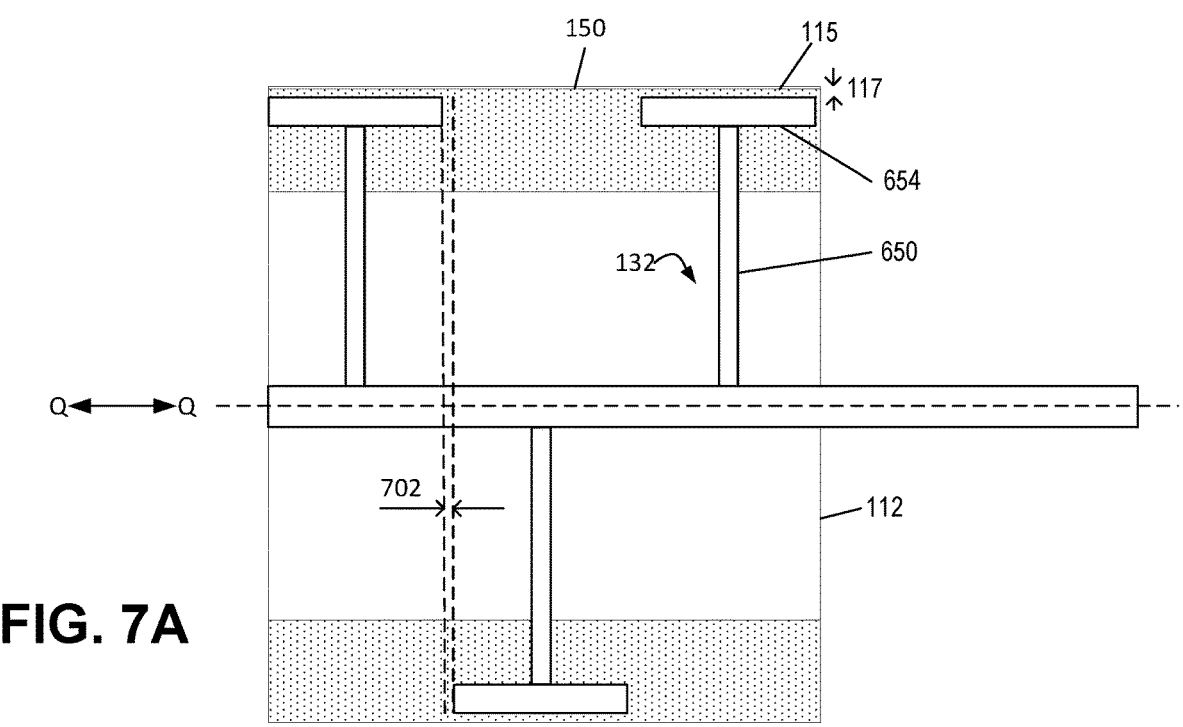
FIGS. 7A and 7B are schematic side views of the reactor systems of FIGS. 1-5 with T-shaped paddles.
Figure 7B:
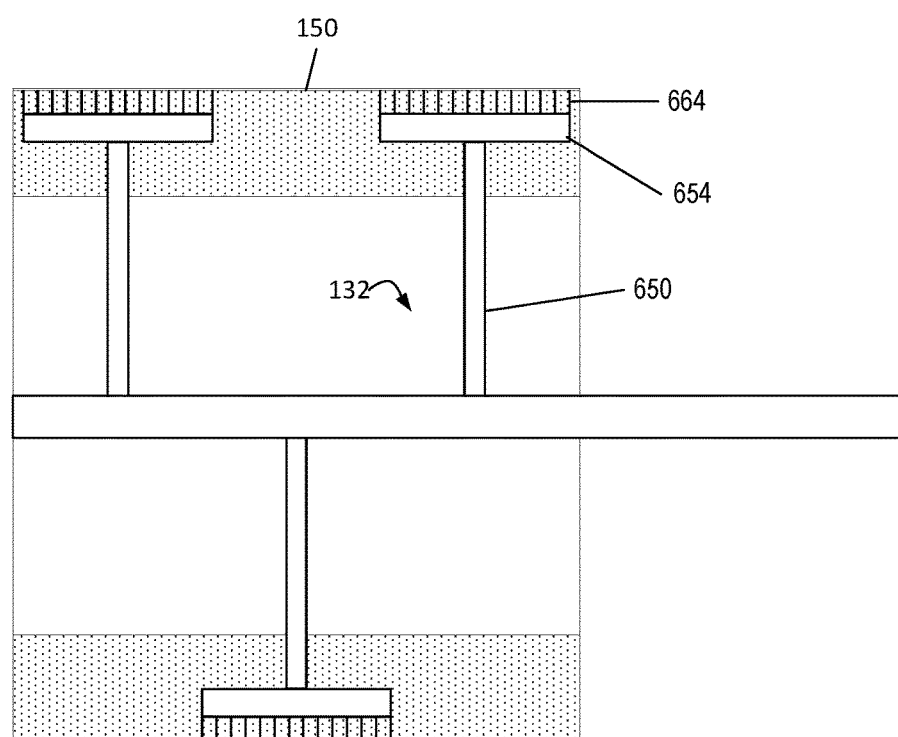

In some implementations, the reactor systems 100, 100', and 100''' described with reference to FIGS. 1-5 can include T-shaped paddles 650. FIGS. 7A and 7B are schematic side views of the reactor systems of FIGS. 1-5 with T-shaped paddles (e.g., T-shaped paddle 650). A gap 117 between a surface 115 of the cross-bar 654 of the T-shaped paddle 650 and an inner surface 150 of the rotary vacuum chamber 112 can be less than a threshold distance (e.g., less than 3 mm).

In some implementations, a spacing 702 of the T-shaped paddles 650 of the paddle assembly 132 along the axial axis Q-Q can be selected such that there is substantially even mechanical agitation and process gas injection across the multiple paddles 650 along the length of the cylindrical portion of the rotary vacuum chamber 112 during rotary motion operation of the paddle assembly 132. In some implementations, spacing 702 can be zero or less than zero (e.g., T-shaped paddles 650 can overlap).

In some implementations, as described with reference to FIG. 7B, T-shaped paddle 650 can include an anti-static brush component 662. FIG. 7B is a schematic side view of the reactor systems of FIGS. 1-5 with T-shaped paddles including anti-static brush components. The anti-static brush component 662 located on the T-shaped paddle 650 of the paddle assembly 132 is in contact with the inner surface 150 of the rotary vacuum chamber 112.

Operation of Reactor System

Figure 8:
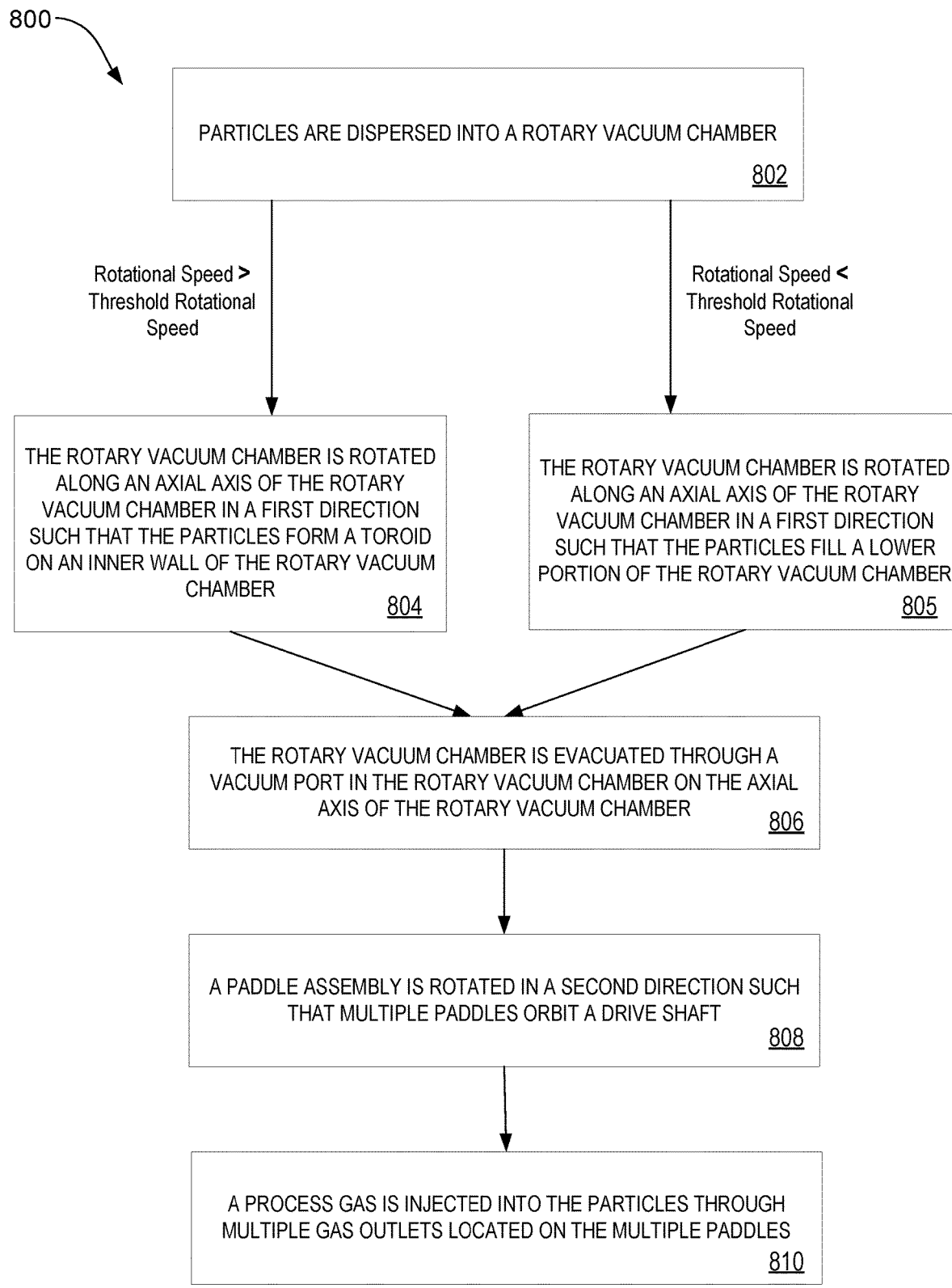
FIG. 8 is a flow diagram of an example process for utilizing the reactor system to coat particles.

FIG. 8 is a flow diagram of an example process of utilizing the reactor system to coat particles. In a first step, particles are dispensed into a rotary vacuum chamber (802). As described with reference to FIGS. 1-7, reactor system (e.g., reactor systems 100, 100', and 100''') include an outer stationary vacuum chamber 110 and inner rotary vacuum chamber 112, where loading ports on each of the stationary vacuum chamber and rotary vacuum chamber (e.g., loading ports 172, 174) can be aligned to allow for loading/unloading of particles to be coated into the reactor system.

The particles (e.g., particles 148) can have a solid core comprising a drug, e.g., one of the drugs discussed above. The solid core can optionally also include an excipient. Once any loading ports (e.g., loading ports 172, 174) are sealed, a controller (e.g., controller 170) operates the reactor system (e.g., reactor systems 100, 100', 100''') according to a recipe in order to form the thin-film metal oxide layers and/or thin polymer layers on the particles.

The rotary vacuum chamber is rotated along an axial axis of the rotary vacuum chamber in a first direction such that the particles form a toroid on an inner wall of the rotary vacuum chamber (804). In some implementations, controller (e.g., controller 170) is configured to operate a drum motor (e.g., drum motor 130a) to generate a rotary motion in the rotary vacuum chamber (e.g., rotary vacuum chamber 112) at a rotational speed that is greater than a threshold rotational speed such that the particles form a toroid on an inner wall 150 of the rotary vacuum chamber 112. A threshold rotation speed can be, for example, a rotational speed of 10 RPM, 12 RPM, 15 RPM, or the like.

In some implementations, a controller is configured to operate a drum motor to generate a rotary motion of the rotary vacuum chamber at a rotational speed of the rotary vacuum chamber that is less than a threshold rotational speed. For a rotational speed less than the threshold rotational speed, the rotary vacuum chamber is rotated along an axial axis of the rotary vacuum chamber in a first direction such that the particles fill a lower portion of the rotary vacuum chamber when the rotary vacuum chamber is rotating in the first direction (805). A rotational speed that is less than a threshold rotational speed can range, for example, between 6-15 RPM. In one example, a lower portion 180 of the rotary vacuum chamber 112 is filled with a particle bed 178 such that as the rotary vacuum chamber 112 rotates in a first direction 152, the particles in the particle bed 178 experience tumbling agitation.

The rotary vacuum chamber is evacuated through a vacuum port in the rotary vacuum chamber aligned on the axial axis of the rotary vacuum chamber (806). In some implementations, vacuum source 134 evacuates the rotary vacuum chamber 112 via the stationary vacuum chamber 110 (e.g., through the filter 176) through the exhaust manifold 136. A low-pressure environment can be established within the rotary vacuum chamber 112, e.g., down to pressures below 1 Torr, e.g., to 1 to 500 mTorr, e.g., 50 mTorr.

A paddle assembly is rotated in a second direction such that a plurality of paddles orbit a drive shaft (808). In some implementations, controller 170 is configured to operate a paddle motor 130b to generate a rotary motion of the paddle assembly 132 in a second direction 160 at a second rotational speed. The second direction of rotation of the paddle assembly 132 can be in a same or opposite direction as the first direction of rotation of the rotary vacuum chamber 112.

The controller 170 can be configured to cause the paddle motor 130b to generate rotary motion of the paddle assembly 132 at rotational speeds up to 200 rpm.

A process gas is injected into the particles through a plurality of gas outlets located on the plurality of paddles (810). In some implementations, the reactor system performs an ALD and/or an MLD thin-film coating process by introducing gaseous precursors of the coating into the rotary vacuum chamber 112. The gaseous precursors are spiked alternatively into the rotary vacuum chamber 112. This permits the deposition process to be a solvent-free process. The half-reactions of the deposition process are self-limiting, which can provide Angstrom or nanometer level control of deposition. In addition, the ALD and/or MLD reaction can be performed at low temperature conditions, such as below 50° C., e.g., below 35° C. Flow rates of the process gas can be selected based on a type of process gas being injected. For example, a flow rate for a $H_2O$ process gas can be 1-2 standard liters per minute (slm) of vaporized precursor for 10 kg of powder. In another example, a flow rate for $H_2O$ process gas could range between 0.5-1 slm for powders with less surface area. In another example, TMA or $TiCl_4$ can have volumetric flow rates, for example, less than 1 slm. In another example, carrier gas flow rates can be, for example, in the 1-3 slm range for 10-15 kg of powder.

Suitable reactants for ALD methods include any of or a combination of the following: monomer vapor, metal-organics, metal halides, oxidants, such as ozone or water vapor, and polymer or nanoparticle aerosol (dry or wet). For example, the first fluid source 138a car provide gaseous trimethylaluminum (TMA) or titanium tetrachloride (TiCl4), whereas the second gas source 138b can provide water. For MLD methods, as an example, the fluid source 138c can provide adipoyl chloride, and the fourth fluid source 138d can provide vaporous or gaseous ethylene diamine.

In some implementations, one of the process gasses flows from the chemical delivery system 122 into the particles 148 through the gas outlets 166 located on the paddles 158 of the paddle assembly 132 as the paddle assembly 132 rotates. Rotation of the paddle assembly 132 agitates the particles to keep them separate, ensuring a large surface area of the particles remains exposed. This permits fast, uniform interaction of the particle surface with the process gas.

For both an ALD process and an MLD process, two reactant gases are alternately supplied to the rotary vacuum chamber 112, with each step of supplying a reactant gas followed by a purge cycle in which the inert gas is supplied to the chamber 112 to force out the reactant gas and by-products used in the prior step.

In some implementations, the reactor system is operated in a continuous flow operation mode, e.g., for an ALD process. During an ALD process, the controller 170 can operate the reactor system (e.g., reactor systems 100, 100', 100''') as follows. In a first reactant half-cycle, while the drum motor 130a rotates the rotary vacuum chamber 112 and paddle motor 130b rotates the paddle assembly 132 to agitate the particles 148:

i) The chemical distribution system 122 is operated to flow the first reactant gas, e.g., TMA, from the source 138a into the rotary vacuum chamber 112 via the gas outlets 166 located on the paddles 158 until the particles 148 (e.g., particle bed 178) are saturated with the first reactant gas. For example, the first reactant gas can flow at a specified flow rate and for a specified period of time, or until a sensor measures a specified first pressure or partial pressure of the first reactant gas in the chamber 112. In some implementations, the first reactant gas is mixed with an inert gas as it flows into the chamber. The specified pressure or partial pressure can be 0.1 Torr to half of the saturation pressure of the reactant gas.

ii) Flow of the first reactant gas is halted, and the vacuum source 134 evacuates the chamber 112, e.g., down to pressures below 1 Torr, e.g., to 1 to 100 mTorr, e.g., 50 mTorr.

These steps (i)-(ii) can be repeated a number of times set by the recipe, e.g., two to ten times.

Next, in a first purge cycle, while the drum motor 130a rotates the rotary vacuum chamber 112 and paddle motor 130b rotates the paddle assembly 132 to agitate the particles 148:

iii) The chemical distribution system 122 is operated to flow only inert gas, e.g., $N_2$, from the source 138e into the chamber 112 via the gas outlets 166 located on the paddles 158 of the paddle assembly 132. The inert gas can flow at a specified flow rate and for a specified period of time, or until a sensor measures a specified second pressure of the inert gas in the chamber 112. The second specified pressure can be 1 to 100 Torr.

iv) The vacuum source 134 evacuates the chamber 112, e.g., down to pressures below 1 Torr, e.g., to 1 to 500 mTorr, e.g., 50 mTorr.

These steps (iii)-(iv) can be repeated a number of times set by the recipe, e.g., six to twenty times.

In a second reactant half-cycle, while the drum motor 130a rotates the rotary vacuum chamber 112 and paddle motor 130b rotates the paddle assembly 132 to agitate the particles 148:

v) The chemical distribution system 122 is operated to flow the second reactant gas, e.g., $H_2O$, from the source 138b into the chamber 112 via the gas outlets 166 located on the paddles 158 of the paddle assembly 132 until the particles 148 are saturated with the second reactant gas. Again, the second reactant gas can flow at a specified flow rate and for a specified period of time, or until a sensor measures a specified third pressure or partial pressure of the second reactant gas in the chamber 112. In some implementations, the second reactant gas is mixed with an inert gas as it flows into the chamber. The third pressure can be 0.1 Torr to half of the saturation pressure of the second reactant gas.

vi) The vacuum source 134 evacuates the chamber 112, e.g., down to pressures below 1 Torr, e.g., to 1 to 500 mTorr, e.g., 50 mTorr.

These steps (v)-(vi) can be repeated a number of times set by the recipe, e.g., two to ten times.

Next, a second purge cycle is performed. This second purge cycle with steps (vii) and (viii) can be identical to the first purge cycle, or can have a different number of repetitions of the steps (iii)-(iv) and/or different specified pressure.

The cycle of the first reactant half-cycle, first purge cycle, second reactant half cycle and second purge cycle can be repeated a number of times set by the recipe, e.g., one to ten times.

The operation is discussed above with an ALD process, but the operation is similar for MLD. In particular, in steps (i) and (v), the reactant gasses are substituted with appropriate process gasses and pressures for deposition of a polymer layer. For example, step (i) can use vaporous or gaseous adipoyl chloride, and step (v) can use are vaporous ethylene diamine.

Moreover, although operation is discussed above with an ALD or MLD process, the system could be used for a chemical vapor deposition (CVD) process. In this case, both reactants are flowed simultaneously into the chamber 110 so as to react inside the chamber, e.g., during step (i). The second reactant half-cycle can be omitted.

In some implementations, the reactor system (e.g., reactor system 100, 100', 100''') is operated in a pulsed flow operation mode, where one or more of the gases (e.g., the reactant gases and/or the inert gas) can be supplied in pulses in which the chamber 112 is filled with the gas to a specified pressure, a delay time is permitted to pass, and the chamber is evacuated by the vacuum source 134 before the next pulse commences.

In particular, for an ALD process, the controller 170 can operate the reactor system 100 as follows.

In a first reactant half-cycle, while the drum motor 130a rotates the rotary vacuum chamber 112 and paddle motor 130b rotates the paddle assembly 132 to agitate the particles 148:

i) The chemical distribution system 122 is operated to flow the first reactant gas, e.g., TMA, from the source 138a into the chamber 112 via the gas outlets 166 located on the paddles 158 of the paddle assembly 132 until a first specified pressure is achieved in the chamber 112. The specified pressure can be 0.1 Torr to half of the saturation pressure of the reactant gas.

ii) Flow of the first reactant gas is halted, and a specified delay time is permitted to pass, e.g., as measured by a timer in the controller. This permits the first reactant to flow through the particles 148 in the rotary vacuum chamber 112 and react with the surface of the particles.

iii) The vacuum source 134 evacuates the chamber 112, e.g., down to pressures below 1 Torr, e.g., to 1 to 100 mTorr, e.g., 50 mTorr.

These steps (i)-(iii) can be repeated a number of times set by the recipe, e.g., two to ten times.

Next, in a first purge cycle, while the drum motor 130a rotates the rotary vacuum chamber 112 and paddle motor 130b rotates the paddle assembly 132 to agitate the particles 148:

iv) The chemical distribution system 122 is operated to flow the inert gas, e.g., $N_2$, from the source 138e into the chamber 112 via the gas outlets 166 located on the paddles 158 of the paddle assembly 132 until a second specified pressure is achieved. The second specified pressure can be 1 to 100 Torr.

v) Flow of the inert gas is halted, and a specified delay time is permitted to pass, e.g., as measured by the timer in the controller. This permits the inert gas to diffuse through the particles in the particle bed 10 to displace the reactant gas and any vaporous by-products.

vi) The vacuum source 132 evacuates the chamber 112, e.g., down to pressures below 1 Torr, e.g., to 1 to 500 mTorr, e.g., 50 mTorr.

These steps (iv)-(vi) can be repeated a number of times set by the recipe, e.g., six to twenty times.

In a second reactant half-cycle, while the drum motor 130a rotates the rotary vacuum chamber 112 and paddle motor 130b rotates the paddle assembly 132 to agitate the particles 148:

vii) The chemical distribution system 122 is operated to flow the second reactant gas, e.g., $H_2O$, from the source 138b into the chamber 112 via the gas outlets 166 located on the paddles 158 of the paddle assembly 132 until a third specified pressure is achieved. The third pressure can be 0.1 Torr to half of the saturation pressure of the reactant gas.

viii) Flow of the second reactant gas is halted, and a specified delay time is permitted to pass, e.g., as measured by the timer in the controller. This permits the second reactant gas to flow through the particles 148 and react with the surface of the particles inside the rotary vacuum chamber 112.

ix) The vacuum source 134 evacuates the chamber 112, e.g., down to pressures below 1 Torr, e.g., to 1 to 500 mTorr, e.g., 50 mTorr.

These steps (vii)-(ix) can be repeated a number of times set by the recipe, e.g., two to ten times.

Next, a second purge cycle is performed. This second purge cycle can be identical to the first purge cycle, or can have a different number of repetitions of the steps (iv)-(vi) and/or different delay time and/or different pressure.

The cycle of the first reactant half-cycle, first purge cycle, second reactant half cycle and second purge cycle can be repeated a number of times set by the recipe, e.g., one to ten times.

Moreover, one or more of the gases (e.g., the reactant gases and/or the inert gas) can be supplied in pulses in which the rotary vacuum chamber 112 is filled with the gas to a specified pressure, a delay time is permitted to pass, and the chamber is evacuated by the vacuum source 134 before the next pulse commences.

The operation is discussed above with an ALD process, but the operation is similar for MLD. In particular, in steps (i) and (vii), the reactant gasses are substituted with appropriate process gasses and pressures for deposition of a polymer layer. For example, step (i) can use vaporous or gaseous adipoyl chloride, and step (vii) can use are vaporous ethylene diamine.

Moreover, although operation is discussed above with an ALD or MLD process, the system could be used for a chemical vapor deposition (CVD) process. In this case, both reactants are flowed simultaneously into the chamber 110 so as to react inside the chamber, e.g., during step (i). The second reactant half-cycle can be omitted.

As noted above, the coating process can be performed at low processing temperature, e.g., below 50° C., e.g., at or below 35° C. In particular, the particles 148 can remain or be maintained at such temperatures during all of steps (i)-(ix) noted above. In general, the temperature of the interior of the reactor chamber does not exceed 35° C. during of steps (i)-(ix). This can be achieved by having the first reactant gas, second reactant gas and inert gas be injected into the chamber at such temperatures during the respective cycles. In addition, physical components of the chamber of the chamber can remain or be maintained at such temperatures, e.g., using a cooling system, e.g., a thermoelectric cooler, if necessary.

In some implementations, the controller can cause the reactor system 100 to first deposit a metal oxide layer on the drug-containing particles, and then deposit a polymer layer over the metal oxide layer on the particles, e.g., using the process described above. In some implementations, the controller can cause the reactor system 100 alternate between depositing a metal oxide layer and depositing a polymer layer on the drug-containing particles, so as to form a multi-layer structure with layers of alternating composition.

The controller 170 and other computing devices part of systems described herein can be implemented in digital electronic circuitry, or in computer software, firmware, or hardware. For example, the controller can include a processor to execute a computer program as stored in a computer program product, e.g., in a non-transitory machine readable storage medium. Such a computer program (also known as a program, software, software application, or code) can be written in any form of programming language, including compiled or interpreted languages, and it can be deployed in any form, including as a standalone program or as a module, component, subroutine, or other unit suitable for use in a computing environment. In some implementations, the controller 105 is a general purpose programmable computer. In some implementations, the controller can be implemented using special purpose logic circuitry, e.g., an FPGA (field programmable gate array) or an ASIC (application specific integrated circuit).

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions. The present disclosure provides apparatus for and methods of preparing pharmaceutical compositions comprising API containing particles encapsulated by one or more layers of metal oxide and/or one or more layers of a polymer. The coating layers are conformal and of controlled thickness from several nanometers to several micrometers in total. The articles to be coated can be composed of only API or a combination of API and one or more excipients. The coating process described herein can provide an API with an increased glass transition temperature for the API relative to uncoated API, a decreased rate of crystallization for an amorphous form of the API relative to uncoated API, and decreased surface mobility of API molecules in the particle compared to uncoated API. Importantly, particle dissolution can be altered. Because the coating is relatively thin, drug products with high drug loading can be achieved. Finally, there are benefits with respect to cost and ease of manufacture because multiple coatings can be applied in the same reactor.

Terms of relative positioning are used to refer to relative positioning of components within the system or orientation of components during operation; it should be understood that the reactor system could be held in a vertical orientation or some other orientation during shipping, assembly, etc.

A number of embodiments of the invention have been described. Nevertheless, it will be understood that various modifications may be made without departing from the spirit and scope of the invention.

What is claimed is:

1. A reactor for coating particles, comprising:
   one or more motors;
   a rotary vacuum chamber configured to hold a plurality of particles to be coated, a cylindrical portion of the rotary vacuum chamber having an inner diameter, and wherein the rotary vacuum chamber is coupled to the one or more motors to rotate the rotary vacuum chamber in a first direction about an axial axis of the cylindrical portion of the rotary vacuum chamber;
   a vacuum port to exhaust gas from the rotary vacuum chamber;
   a paddle assembly including a rotatable drive shaft extending through the rotary vacuum chamber along the axial axis of the rotary vacuum chamber and a plurality of paddles each extending radially from the drive shaft,
      wherein the rotatable drive shaft is coupled to the one or more motors such that rotation of the drive shaft by the one or more motors orbits the plurality of paddles about the drive shaft in a second direction, wherein the plurality of paddles are equally angularly spaced about the axial axis,
      wherein the paddle assembly includes gas outlets, and
      wherein the paddle assembly includes chemical supply passages to deliver a process gas via the gas outlets into the plurality of particles; and
   a controller configured to cause the one or more motors to rotate the rotary vacuum chamber in the first direction about the axial axis of the cylindrical portion of the rotary vacuum chamber at a rotation speed such that a portion of the plurality of particles provide a particle bed that remains in a lower portion of the rotary vacuum chamber,
      wherein the gas outlets are positioned on the plurality of paddles at a distance from an inner surface of the rotary vacuum chamber such that, in operation as the plurality of paddles orbit, at least one gas outlet is located within the particle bed formed by the plurality of particles to percolate the process gas through the plurality of particles held within the rotary vacuum chamber.

2. The reactor of claim 1, wherein rotation in the first direction is in a same direction of rotation as the rotation in the second direction.

3. The reactor of claim 1, wherein the gas outlets are located on a trailing edge of the plurality of paddles.

4. The reactor of claim 1, wherein a vacuum port is located in-line with the axial axis of the rotary vacuum chamber.

5. The reactor of claim 1, wherein the plurality of paddles are configured to sweep along an entirety of a length of the rotary vacuum chamber along the axial axis of the rotary vacuum chamber.

6. The reactor of claim 1, wherein the plurality of paddles further comprise anti-static brushes located between outer edges of the paddles and in contact with the inner surface of the inner diameter of the rotary vacuum chamber.

7. The reactor of claim 1, further comprising a port to deliver particles to or receive particles from the rotary vacuum chamber.

8. The reactor of claim 1, wherein the axial axis of the rotary vacuum chamber is oriented horizontally relative to gravity.

9. The reactor of claim 1, wherein rotation in the first direction is in an opposite direction of rotation as the rotation in the second direction.

10. The reactor of claim 1, wherein each paddle of the plurality of paddles comprises a base shaft coupled to the drive shaft and a plate portion that is wider than the base shaft and located on an end of the base shaft opposite a surface where the base shaft is coupled to the drive shaft,
      wherein an outer edge of the paddle is separated from an inner surface of the rotary vacuum chamber, and
      wherein the chemical supply passages deliver the process gas through the base shaft and plate portion of the paddle.

11. The reactor of claim 10, wherein at least one gas outlet of the gas outlets is located on the plate portion of the paddle of the plurality of paddles.

12. The reactor of claim 10, wherein the plurality of paddles are spaced along the axial axis such that a portion of a respective plate portion of each paddle overlaps laterally along the axial axis with at least one other portion of another plate portion of another paddle of the plurality of paddles.

13. A reactor for coating particles, comprising:
   one or more motors;
   a rotary vacuum chamber configured to hold a plurality of particles to be coated, a cylindrical portion of the rotary vacuum chamber having an inner diameter, and wherein the rotary vacuum chamber is coupled to the one or more motors;
   a controller configured to cause the one or more motors to rotate the rotary vacuum chamber in a first direction about an axial axis of the cylindrical portion of the rotary vacuum chamber at a rotation speed such that the particles undergo tumbling agitation;
   a vacuum port to exhaust gas from the rotary vacuum chamber; and
   a paddle assembly including a rotatable drive shaft extending through the rotary vacuum chamber along the axial axis of the rotary vacuum chamber and a plurality of paddles extending radially from the drive shaft,
      wherein the rotatable drive shaft is coupled to the one or more motors such that rotation of the drive shaft by the one or more motors orbits the plurality of paddles about the drive shaft in a second direction, wherein the plurality of paddles are equally angularly spaced about the axial axis, wherein the paddle assembly includes gas outlets, and wherein the paddle assembly includes chemical supply passages to deliver a process gas via the gas outlets into the plurality of particles, wherein the gas outlets are positioned on the plurality of paddles at a distance from an inner surface of the rotary vacuum chamber such that, in operation as the plurality of paddles orbit, at least one gas outlet is located within a particle bed formed by the plurality of particles to percolate the process gas through the plurality of particles held within the rotary vacuum chamber.

14. The reactor of claim 13, wherein the controller is configured to cause the one or more motors to rotate the rotary vacuum chamber about the axial axis at the rotation speed that is less than 6 RPM.

15. The reactor of claim 13, wherein the rotation speed of the drive shaft relative to the rotary vacuum chamber about the axial axis is less than 6 rpm.

16. The reactor of claim 13, further comprising a stationary vacuum chamber, wherein the rotary vacuum chamber is disposed within the stationary vacuum chamber.

17. The reactor of claim 16, further comprising a vacuum pump coupled to the stationary vacuum chamber and coupled to the vacuum port to exhaust gas from the rotary vacuum chamber.

18. The reactor of claim 16, wherein the the one or more motors are coupled to the stationary vacuum chamber.

19. The reactor of claim 16, wherein the rotary vacuum chamber further comprises a surface of the inner diameter of the rotary vacuum chamber having horizontal or angled baffles.

20. The reactor of claim 13, comprising a base to support the reactor on a mounting surface, and wherein the rotary vacuum chamber is secured to the base such that the axial axis will be perpendicular to the mounting surface.

21. The reactor of claim 13, comprising a base to support the reactor on a mounting surface, and wherein the rotary vacuum chamber is secured to the base such that the axial axis will be parallel to the mounting surface.

* * * * *

UNITED STATES PATENT AND TRADEMARK OFFICE
CERTIFICATE OF CORRECTION

Page 1 of 1

PATENT NO. : 11,174,552 B2
APPLICATION NO. : 16/438371
DATED : November 16, 2021
INVENTOR(S) : Neikirk et al.

It is certified that error appears in the above-identified patent and that said Letters Patent is hereby corrected as shown below:

On the Title Page

Column 2, Line 2, under Other Publications, delete "PCT/US2019/03672I" and insert --PCT/US2019/036721-- therefor.

In the Claims

Column 26, Line 8, in Claim 18, delete "the the" and insert --the-- therefor.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*